US008012726B2

(12) United States Patent
Wang et al.

(10) Patent No.: US 8,012,726 B2
(45) Date of Patent: Sep. 6, 2011

(54) METHOD OF MAKING BIOETHANOL BY USING GLUCOSE ISOMERASE MUTANTS

(75) Inventors: Jun Wang, Hong Kong Science Park (HK); Rongzhao Fu, Hong Kong Science Park (HK); Tin Cho Cheung, Hong Kong Science Park (HK)

(73) Assignee: BioRight Worldwide Company Limited, Tortola (VG)

( * ) Notice: Subject to any disclaimer, the term of this patent is extended or adjusted under 35 U.S.C. 154(b) by 488 days.

(21) Appl. No.: 12/093,881

(22) PCT Filed: Oct. 30, 2006

(86) PCT No.: PCT/CN2006/002902
§ 371 (c)(1),
(2), (4) Date: Oct. 14, 2008

(87) PCT Pub. No.: WO2007/056931
PCT Pub. Date: May 24, 2007

(65) Prior Publication Data
US 2009/0221048 A1    Sep. 3, 2009

(30) Foreign Application Priority Data
Nov. 18, 2005    (CN) .......................... 2005 1 0123630

(51) Int. Cl.
*C12P 7/06*    (2006.01)
*C12N 9/00*    (2006.01)
*C12N 9/90*    (2006.01)
*C12N 1/20*    (2006.01)
*C12N 15/00*   (2006.01)
*C07H 21/04*   (2006.01)

(52) U.S. Cl. ..... 435/161; 435/183; 435/233; 435/252.3; 435/320.1; 536/23.2

(58) Field of Classification Search .................. None
See application file for complete search history.

(56) References Cited

U.S. PATENT DOCUMENTS

| | | | |
|---|---|---|---|
| 5,656,497 | A | 8/1997 | Zeikus et al. |
| 6,475,768 | B1 | 11/2002 | Otero et al. |
| 2008/0113415 | A1 | 5/2008 | Wang et al. |

FOREIGN PATENT DOCUMENTS

| | | |
|---|---|---|
| CN | 1213003 | 4/1999 |
| CN | 1693473 | 11/2005 |
| CN | 1693473 A | 11/2005 |
| CN | 1743454 | 3/2006 |
| CN | 1702172 | 11/2008 |
| EP | 0351029 | 1/1990 |
| EP | 1264883 | 12/2002 |
| JP | 2000333684 | 12/2000 |
| WO | 00/61733 A1 | 10/2000 |
| WO | WO 2005116217 A1 * | 12/2005 |

OTHER PUBLICATIONS

Lonn et al., "Cold Adaptation of Xylose Isomerase from Thermus Thermophilus Through Random PCR Mutagenesis; Gene Cloning and Protein Characterization"; Eur. J. Biochem; 2002; pp. 157-163; vol. 269.
Bhosale et al.; "Molecular and Industrial Aspects of Glucose Isomerase"; Microbiological Reviews, Jun. 1996; pp. 280-300; vol. 60; No. 2.
Kaneko et al., "Characterization of Acid-Stable Glucose Isomerase from *Streptomyces* sp., and Dedvelopment of Single-Step Processes for High-Fructose Corn Sweetener (HFCS) Production", Biosci. Biotechnol. Biochem. 2000, pp. 940-947, vol. 64(5).
Lee et al., "Cloning, Sequencing and Biochemical Characterization of Xylose Isomerase from *Thermoanaerobacterium saccharolyticum* Strain B6A-RI", J. of General Microbiology, 1993, pp. 1227-1234, vol. 139.
Vieille et al., "Xylose Isomerases from Thermotoga", Methods in Enzymology, 2001, pp. 215-224, vol. 330.
Lee et al., "Genetic Organization Sequence and Biochemical Characterization of Recombinant B-xylosidase from *Thermoanaerobacterium saccharolyticum* strain B6A-RI", J. of General Microbiology, 1993, pp. 1235-1243, vol. 139.
Sriprapundh et al., "Molecular Determinants of Xylose Isomerase Thermal Stability and Activity: Analysis of Thermozymes by Site-Directed Mutagenesis", Protein Engineering, 2000, pp. 259-265, vol. 13(4).
Sriprapundh et al., Directed Evolution of Thermotoga Neapolitana Xylose Isomerase: High Activity on Glucose at Low Temperature and Low pH, Protein Engineering, 2003, pp. 683-690, vol. 16(9).
IUPAC-IUB Joint Commission on Biochemical Nomenclature (JCBN), "Nomenclature and Symbolism for Amino Acids and Peptides", Eur. J. Biochem., 1984, pp. 9-37, vol. 138.
Ho et al., "Site-Directed Mutagenesis by Overlap Extension Using the Polymerase Chain Reaction", Gene, 1989, pp. 51-59, vol. 77.
White, "PCR Protocols: Current Methods and Applications", Methods in Molecular Biology, 1993, pp. 277-286, vol. 15.
Dische et al., "A New Spectrophotometric Method for the Detecton and Determination of Keto Sugars and Trioses", 1951, pp. 583-587, vol. 192.
Nakamura, "Determination of Fructose in the Presence of a Large Excess of Glucose—Part V—A Modified Cysteine-Carbazole Reaction", Agr. Biol. Chem., 1968, pp. 701-706, vol. 32(6).

* cited by examiner

*Primary Examiner* — Christian Fronda
(74) *Attorney, Agent, or Firm* — The Webb Law Firm

(57) ABSTRACT

This invention provides use of a series of recombinant *Thermoanaerobacterium saccharolyticum* glucose isomerases with improved catalytic activity obtained by using recombinant techniques. These mutants comprise at least one amino acid variation at position 87, position 139, position 182, position 187, position 217, position 260, position 276, or position 299, and can be used in the conversion of hemicellulose to ethanol.

1 Claim, 1 Drawing Sheet

METHOD OF MAKING BIOETHANOL BY USING GLUCOSE ISOMERASE MUTANTS

FIELD OF THE INVENTION

The present invention relates to molecular biology, and specifically relates to recombinant glucose isomerases with improved activity or both of improved activity and thermostability, the method of preparing the same using recombinant techniques, and use of the same.

BACKGROUND OF THE INVENTION

Glucose isomerase (E.C.5.3.1.5 or xylose isomerase) is a key enzyme in the pentose phosphate pathway. It is one of the most important industrial enzymes (Kaneko et al., *Bioscience, Biotechnology, and Biochemistry* 2000, 64:940-947). In bio-energy industry, people are trying to use the enzyme, together with other key enzymes in the degradation pathway of cellulose and hemicelluloses, to produce bioethanol commercially. For example, the pathway of the enzymatic degradation of xylan to xylulose-5-phosphate is as follows: xylan is converted into xylo-oligosaccharides in the presence of β-1,4-xylanase, xylo-oligosaccharides is further turned into xylose by β-xylosidase. Then, xylose is converted to xylulose by glucose isomerase (xylose isomerase) and xylulose is converted to xylulose-5-phosphate by β-xylulokinase.

Under the pressure of environmental pollution and the shortage of oil, many countries in the world, such as Brazil, the United States and Canada have been using sugar cane or corn as starting materials to produce fuel ethanol. China has also been using corn or other crops to produce bioethanol. As biomass is very rich in the world, scientists in different countries are exploring ways to use cellulose- and hemicellulose-rich agricultural residues to produce bioethanol industrially. Glucose isomerase is a key enzyme in the biodegradation of hemicellulose. With high activity, or with both of high activity and thermostability glucose isomerase can efficiently reduce the cost of bioethanol production to facilitate industrial production of bioethanol.

Scientists around the world have been working on the identification of thermostable and highly active glucose isomerases from thermophilic bacteria, and production of the same via protein engineering. J. G. Zeikus and his collaborators isolated and studied thermostable glucose isomerases from thermophilic bacteria, such as *Thermoanaerobacterium saccharolyticum* and *Thermotoga neapolitana* (Lee et al., *Journal of General Microbiology*, 139:1227-1234, 1993; Vieille et al., *Methods in Enzymology*, 330:215-24, 2001; Lee et al., *Journal of General Microbiology*, 139:1241-1243, 1993; Scriprapundh et al., *Protein Engineering*, 13:259-265, 2000; Scriprapundh et al., *Protein Engineering*, 16:683-690, 2003; Zeikus et al., U.S. Pat. No. 5,656,497). Nevertheless, the thermostabilities of the thermostable glucose isomerases from these and other bio-resources are still much to be desired as the activities thereof are low, and thus are not applicable to industrial applications. Therefore, glucose isomerase with high activity, or high activity and thermostability remains desirable.

SUMMARY OF THE INVENTION

The inventors of the present invention have studied the activity of a series of mutants obtained by genetic and protein engineering of *Thermoanaerobacterium saccharolyticum* glucose isomerase. Thus, the present invention provides the use of glucose isomerase mutants with improved catalytic activity in the conversion of D-xylose to D-xylulose under high temperature.

The inventors of the present invention have introduced mutations, by site-directed mutagenesis, into the *T. saccharolyticum* glucose isomerase gene and obtained a series of highly active or highly active and thermostable glucose isomerase mutants after screening on MacConkey agar. More specifically, the molecular biotechniques being used to generate glucose isomerase mutants include: construction of plasmid carrying the wild-type glucose isomerase gene; design of mutation sites and the mutated amino acids; design of appropriate primers; PCR amplification of DNA fragments using the wild-type glucose isomerase gene or its derivative as template; assembly of the DNA fragments; PCR amplification of the full-length glucose isomerase genes containing the mutation(s); cloning of the mutant genes into appropriate vectors; transformation of the vectors containing the genes into appropriate host cells; screening of the transformants for clones carrying desired glucose isomerase mutants; isolation of the plasmid DNA from the positive clones; and carrying out DNA sequencing to verify the mutations. Finally, the activity of the mutated isomerase is assessed using D-xylose as substrate, and mutated isomerase with higher catalytic activity than that of the wild-type is selected. The selected isomerase is used in conversion of D-xylose to D-xylulose, degradation of hemicellulose and the production of bioethanol.

For the preparation of the novel glucose isomerases in this invention, suitable vectors include but are not limited to prokaryotic expression vectors pGEMT-Easy, pRSET and pET21; include but are not limited to eukaryotic expression vectors pYD1 and pYES2/GS; include but are not limited to cloning vectors pUC18/19 and pBluescript-SK.

For the preparation of the glucose isomerase mutants in this invention, the mutated glucose isomerase gene can be expressed intra-cellularly in prokaryotic or eukaryotic cells, or can be expressed extra-cellularly in prokaryotic or eukaryotic cells by using any other techniques known in the art.

For the preparation of the novel glucose isomerases in this invention, the host cells can be prokaryotic or eukaryotic cells. The prokaryotic cells include but are not limited to *E. coli, Bacillus subtilis, Bacillus brevis, Bacillus megaterium* (e.g. *B. megaterium* BP931), *T. saccharolyticum* and *Streptomyces* (erg. *S. diastaticus* M1033). The eukaryotic cells include but are not limited to *Saccharomyces cerevisiae* and *Pichia pastoris* (e.g. *P. pastoris* GS115/9891).

The glucose isomerase mutants according to this invention, using Sequence 2 in the Sequence Listing as the reference sequence, comprise at least one mutation, or at least two mutations, or at least three mutations, or at least four mutations, or at least five mutations, or at least six mutations or at least seven mutations at position(s) selected from 87, 139, 182, 187, 217, 260, 276 and 299. And the glucose isomerase mutants have a catalytic activity at least 50% higher than the wild-type in the reaction of xylulose generation using D-xylose as substrate. The glucose isomerase mutants can be used in the degradation of hemicellulose and the production of bioethanol.

Using Sequence 2 in the Sequence Listing as reference, preferably, the amino acid phenylalanine (Phe) at position 87 is mutated to methionine (Met), or leucine (Leu); tryptophan (Trp) at position 139 is mutated to serine (Ser), or lysine (Lys), or cysteine (Cys), or isoleucine (Ile), or threonine (Thr), or asparagine (Asn), or aspartic acid (Asp); arginine (Arg) at position 182 is mutated to alanine (Ala), or proline (Pro), or serine (Ser), or isoleucine (Ile), or threonine (Thr), or valine (Val); valine (Val) at position 187 is mutated to glycine (Gly), or alanine (Ala), or proline (Pro); valine (Val) at position 217 is mutated to arginine (Arg), or glycine (Gly); aspartic acid (Asp) at position 260 is mutated to glutamic acid (Glu), or alanine (Ala); phenylalanine (Phe) at position 276 is mutated to glycine (Gly), or threonine (Thr); and/or threonine (Thr) at position 299 is mutated to isoleucine (Ile), or tyrosine (Tyr), or cysteine (Cys), or methionine (Met), or glutamic acid (Glu).

More preferably, the amino acid sequences of the mutants according to this invention comprise any one of the Sequence 5 to Sequence 40 (corresponding to SEQ ID NO.:5 to SEQ ID NO.: 40) as listed in the Sequence Listing.

Most preferably, the glucose isomerase mutants according to this invention comprise the mutated amino acid sequences in Table 2. The glucose isomerase mutants obtained in this invention possess both of high catalytic activity and thermostability. For example, a seven-mutation mutant MGI4-34 possesses an activity 305.9% higher than that of wild-type and still has 50% or more of the original catalytic activity after heat treatment at 80° C. for 19.2 hours. Another seven-mutation mutant MGI4-35 possesses an activity 296.3% higher than that of wild-type and still has 50% or more of the original catalytic activity after heat treatment at 80° C. for 24 hours.

The glucose isomerase mutants according to this invention can be used in an unpurified crude enzyme form, or in a partially purified enzyme form, or in a completely purified enzyme preparation. If required, the glucose isomerase mutants can be prepared as immobilized enzyme, or immobilized cells using known immobilization methodologies. The vector with the expressed glucose isomerase mutant can be transformed into bacteria, such as *Klebsiella oxytoca* and *Zymomonas mobilis, Saccharomyces*, or other hosts, such as *Pichia pastoris*, to speed up the metabolism of xylose. Specifically, the expression bacteria of the glucose isomerase mutants included natural or engineered bacteria for bioethanol fermentation, such as *Klebsiella oxytoca* and *Zymomonas mobilis*; natural or engineered *Saccharomyces* for bioethanol fermentation; natural or engineered *Pichia pastoris* for bioethanol fermentation.

DEFINITIONS

Term "wild-type" as used herein refers to the glucose isomerase from *Thermoanaerobacterium saccharolyticum* ATCC 49915, with its DNA sequence as Sequence 1 in the Sequence Listing, with its amino acid sequence as Sequence 2 in the Sequence Listing. The DNA sequence of the wild-type glucose isomerase in this invention is different in two nucleotides from the published DNA sequence of a glucose isomerase from the same species (Lee et al., *Journal of General Microbiology*, 139:1227-1234, 1993; GenBank L09699); namely, the nucleotides of the wild-type glucose isomerase in this invention at position 241-242 are GC, coding alanine (Ala) at position 81; while the corresponding nucleotides in GenBank L09699 are CG, coding arginine (Arg) at position 81.

Term "reference sequence" as used herein refers to Sequence 1 in the Sequence Listing when it is a DNA sequence; or Sequence 2 in the Sequence Listing when it is an amino acid sequence. The alignment of the reference sequence and the sequences of the glucose isomerase mutants can be done manually or by computer (e.g. using computer softwares CLUSTALW, AMAS, DIALIGN, etc.).

Term "position" or "position x", where x is a numeral, as used herein refers to the position of the nucleotide or amino acid of the mutant sequence in the corresponding reference sequence when the alignment between the glucose isomerase mutants of the present invention and the wild-type glucose isomerase reaches maximum in homology.

Term "glucose isomerase mutant" as used herein refers to an enzyme using Sequence 2 in the Sequence Listing as the reference sequence contains at least one mutation at position 87, position 139, position 182, position 187, position 217, position 260, position 276 or position 299 and has a catalytic activity at least 50% higher than that of the wild-type glucose isomerase in the reaction of xylulose using D-xylose as substrate. Therefore, in the present invention, the glucose isomerase mutants include mutants with an amino acid sequence that is the same as Sequence 4 in the Sequence Listing, or is a conservative substitution of Sequence 4, or is Sequence 4 with addition, or deletion of one or several amino acids, or is Sequence 4 with amino terminal or carboxyl terminal deletion, or comprises partial or complete repetition of Sequence 4. IUPAC nomenclature and symbolism for amino acid abbreviations are used in the present invention (*European Journal of Biochemistry*, 138:9-37, 1984).

DESCRIPTION OF THE PREFERRED EMBODIMENT

Figure 1:
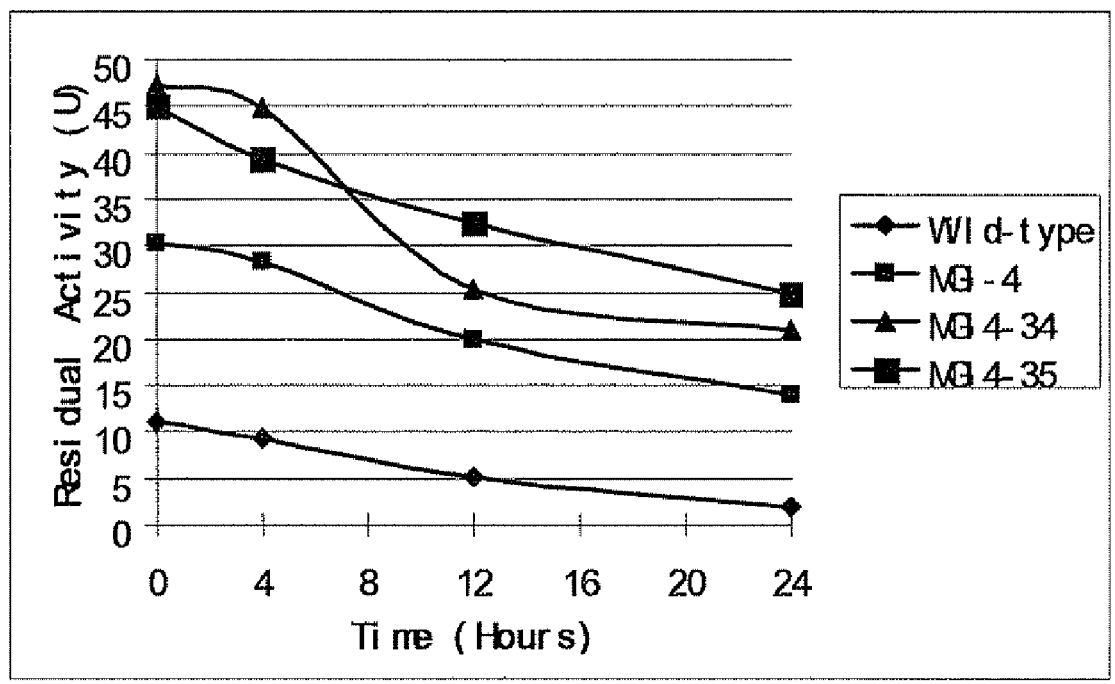
FIG. 1 shows the thermal stability of the wild-type glucose isomerase and glucose isomerase mutants MGI-4, MGI4-34 and MGI4-35 at 80° C. Details are described in Examples 9 and 15.

The examples presented below are for illustration of the invention only and are not intended to be regarded as the limitation of the invention. In the following examples, conventional practice or manufacturers' suggestion/protocol was followed in cases where the conditions were not specified.

Example 1

Amplification of Wild-Type Glucose Isomerase and Construction of pGEMT-TS

Primers T1 and T2 (Table 1) were designed based on the sequence of GenBank L09699 and used to amplify the wild-type glucose isomerase gene from *T. saccharolyticum* ATCC 49915 (ATCC, USA).

The amplification condition was: 20 mM Tris-HCl (pH 8.8), 10 mM KCl, 10 mM $(NH_4)_2SO_4$, 2 mM $MgSO_4$, 0.1% Triton X-100, 50 μM dATP, 50 μM dTTP, 50 μM dCTP, 50 μM dGTP, 400 nM primer T1, 400 nM primer T2, 1.5 U Taq DNA polymerase (Promega, USA), a loopful of *T. saccharolyticum* colony, and the total volume was adjusted to 50 μl with sterile distilled water.

The PCR amplification program for the reaction was: 95° C., 3 min; then 40 cycles of 95° C., 50 sec, 50° C., 30 sec, 72° C., 1 min; and finally 72° C., 10 min. The amplified PCR product, about 1.5 kb in length, was ligated into vector pGEMT-Easy to generate pGEMT-TS. The pGEMT-TS was sequenced to determine the DNA sequence of the wild-type glucose isomerase as Sequence 1 in the Sequence Listing and the corresponding amino acid sequence as Sequence 2 in the Sequence Listing. The DNA sequence of the wild-type glucose isomerase is different from that of the published DNA sequence of a glucose isomerase from the same species (GenBank L09699) where the nucleotides of the wild-type glucose isomerase in this invention at position 241-242 are GC, coding alanine (Ala) at the amino acid position 81; while the corresponding nucleotides in GenBank L09699 are CG, coding arginine (Arg) at the position 81.

Example 2

Site-Directed Mutagenesis of Trp139 of Wild-Type Glucose Isomerase

The site directed mutagenesis was done as described by Ho et al., *Gene* 77:51-59, 1989 and White et al., *PCR protocol: current methods and applications*. Totowa, N.J.: Humana Press 1993.

With pGEMT-TS (Example 1) as template, the Trp (W) at position 139 of the wild-type glucose isomerase was mutated to Phe (F) to generate glucose isomerase mutant MGI-W139F by PCR amplification using primers 139FF and 139FR (Table 1) and universal primers T1 and T2 (Example 1).

Fragment T1FR was amplified using primer pair T1 and 139FR. Fragment FFT2 was amplified using primer pair 139FF and T2. The amplification condition was: 20 mM Tris-HCl (pH 8.8), 10 mM KCl, 10 mM $(NH_4)_2SO_4$, 2 mM $MgSO_4$, 0.1% Triton X-100, 50 µM dATP, 50 µM dTTP, 50 µM dCTP, 50 µM dGTP, 400 nM primer T1 and 400 nM primer 139FR (for fragment T1FR) or 400 nM primer T2 and 400 nM primer 139FF (for fragment FFT2), 1.5 U Pfu DNA polymerase (Promega, USA), 20 ng pGEMT-TS, and the total volume was adjusted to 50 µl with sterile distilled water. The PCR amplification program for the reaction was: 95° C., 3 min; then 35 cycles of 95° C., 50 sec 52° C., 30 sec, 72° C., 3 min; and finally 72° C., 5 min. The PCR products, fragment T1FR and fragment FFT2, were separated on 1% agarose gel and recovered using QIAquick Gel Extraction Kit (QIAGEN, German). The full-length glucose isomerase gene was then assembled on the following condition: 20 mM Tris-HCl (pH 8.8), 10 mM KCl, 10 mM $(NH_4)_2SO_4$, 2 mM $MgSO_4$, 0.1% Triton X-100, 50 µM dATP, 50 µM dTTP, 50 µM dCTP, 50 µM dGTP, 400 nM primer T1 and 400 nM primer T2, 1.5 U Pfu DNA polymerase, 20 ng fragment T1ER and 20 ng fragment FFT2, and the total volume was adjusted to 50 µl with sterile distilled water. The PCR amplification program for the reaction was: 95° C., 3 min; then 35 cycles of 95° C., 50 sec, 52° C., 30 sec, 72° C., 3 min; and finally 72° C., 5 min. The full-length mutant MGI-W139F was separated on 1% agarose gel and recovered using QIAquick Gel Extraction Kit. Plasmid pGEMT-MGI-W139F, generated after ligation of MGI-W139F into pGEMT-Easy, was transformed into competent *E. coli* HB101 and the transformants were screened for glucose isomerase activity on 1% MacConkey plates containing 1% D-xylose and 50 mg/L ampicillin. Plasmid pGEMT-MGI-W139F DNA was then isolated from positive clones and sequenced. The amino acid sequence of MGI-W139F is shown as Sequence 5 in the Sequence Listing and the specific activity thereof is shown in Table 2.

Example 3

Site-Directed Mutagenesis of Arg182 of Glucose Isomerase

The site directed mutagenesis was done as described by Ho et al., *Gene* 77:51-59, 1989 and White et al., *PCR protocol: current methods and applications*. Totowa, N.J.: Humana Press 1993.

Using pGEMT-TS (Example 1) as template, the Arg (R) at position 182 of the wild-type glucose isomerase was mutated to Ala (A) to generate glucose isomerase mutant MGI-R182A by PCR amplification with site-directed primers 182AF and 182AR (Table 1) and universal primers T1 and T2 (Example 1).

Fragment T1AR was amplified using primer pair T1 and 182AR. Fragment AFT2 was amplified using primer pair 182AF and T2. The amplification condition was: 20 mM Tris-HCl (pH 8.8), 10 mM KCl, 10 mM $(NH_4)_2SO_4$, 2 mM $MgSO_4$, 0.1% Triton X-100, 50 µM dATP, 50 µM dTTP, 50 µM dCTP, 50 µM dGTP, 400 nM primer T1 and 400 nM primer 182AR or 400 nM primer T2 and 400 nM primer 182AF, 1.5 U Pfu DNA polymerase, 20 ng pGEMT-TS, and the total volume was adjusted to 50 µl with sterile distilled water. The PCR amplification program for the reaction was: 95° C., 3 min; then 35 cycles of 95° C., 50 see, 52° C., 30 see, 72° C., 3 min, and finally 72° C., 5 min. The PCR products, fragment T1AR and fragment AFT2, were separated on 1% agarose gel and recovered using QIAquick Gel Extraction Kit. The full-length glucose isomerase gene was then assembled on the following condition: 20 mM Tris-HCl (pH 8.8), 10 mM KCl, 10 mM $(NH_4)_2SO_4$, 2 mM $MgSO_4$, 0.1% Triton X-100, 50 µM dATP, 50 µM dTTP, 50 µM dCTP, 50 µM dGTP, 400 nM primer T1 and 400 nM primer T2, 1.5 U Pfu DNA polymerase, 20 ng fragment T1AR and 20 ng fragment AFT2, and the total volume was adjusted to 50 µl with sterile distilled water. The PCR amplification program for the reaction was: 95° C., 3 min; then 35 cycles of 95° C., 50 sec, 52° C., 30 sec, 72° C., 3 min; and finally 72° C., 5 min. The full-length mutant MGI-R182A was separated on 1% agarose gel and recovered using QIAquick Gel Extraction Kit. Plasmid pGEMT-MGI-R182A, generated after ligation of MGI-R182A into vector pGEMT-Easy, was transformed into competent *E. coli* HB101 and the transformants were screened for glucose isomerase activity on 1% MacConkey plates containing 1% D-xylose and 50 mg/L ampicillin. Plasmid pGEMT-MGI-R182A DNA was then isolated from positive clones and sequenced. The amino acid sequence of MGI-R182A is shown as Sequence 6 in the Sequence Listing.

Example 4

Site-Directed Mutagenesis of Phe187 of Glucose Isomerase

The site directed mutagenesis was done as described by Ho et al., *Gene* 77:51-59, 1989 and White et al., *PCR protocol: current methods and applications*. Totowa, N.J.: Humana Press 1993.

Using pGEMT-TS (Example 1) as template, the Phe (F) at position 187 of the wild-type glucose isomerase was mutated to Ser (S) to generate glucose isomerase mutant MGI-F187S by PCR amplification with site-directed primers 187SF and 187SR (Table 1) and universal primers T1 and T2 (Example 1).

Fragment T1SR was amplified using primer pair T1 and 187SR, Fragment SFT2 was amplified using primer pair 187SF and T2. The amplification condition was: 20 mM Tris-HCl (pH 8.8), 10 mM KCl, 10 mM $Q)_2SO_4$, 2 mM $MgSO_4$, 0.1% Triton X-100, 50 µM dATP, 50 µM dTTP, 50 µM dCTP, 50 µM dGTP, 400 nM primer T1 and 400 nM primer 187SR or 400 nM primer T2 and 400 nM primer 187SF, 1.5 U Pfu DNA polymerase, 20 ng pGEMT-TS, and the total volume was adjusted to 50 µl with sterile distilled water. The PCR amplification program for the reaction was: 95° C., 3 min; then 35 cycles of 95° C., 50 sec, 52° C., 30 sec, 72° C., 3 min; and finally 72° C., 5 min. The PCR products, fragment T1SR and fragment SFT2, were separated on 1% agarose gel and recovered using QIAquick Gel Extraction Kit. The full-length glucose isomerase gene was then assembled on the following condition: 20 mM Tris-HCl (pH 8.8), 10 mM KCl, 10 mM (NH$_4$)$_2$SO$_4$, 2 mM MgSO$_4$, 0.1% Triton X-100 150 µM dATP, 50 µM dTTP, 50 µM dCTP, 50 µM dGTP, 400 nM primer T1 and 400 nM primer T2, 1.5 U Pfu DNA polymerase, 20 ng fragment T1SR and 20 ng fragment SFT2, and the total volume was adjusted to 50 µl with sterile distilled water. The PCR amplification program for the reaction was: 95° C., 3 min; then 35 cycles of 95° C., 50 see, 52° C., 30 sec, 72° C., 3 min; and finally 72° C., 5 min. The full-length mutant MGI-F187S was separated on 1% agarose gel and recovered using QIAquick Gel Extraction Kit. Plasmid pGEMT-MGI-F187S, generated after ligation of MGI-F187S into vector pGEMT-Easy, was transformed into competent *E. coli* HB101 and the transformants were screened for glucose isomerase activity on 1% MacConkey plates containing 1% D-xylose and 50 mg/L ampicillin. Plasmid pGEMT-MGI-F187S DNA was then isolated from positive clones and sequenced. The amino acid sequence of MGI-F187S is shown as Sequence 7 in the Sequence Listing.

Example 5

Site-Directed Mutagenesis of Thr299 of Glucose Isomerase

The site directed mutagenesis was done as described by Ho et al., *Gene* 77:51-59, 1989 and White et al., *PCR protocol: current methods and applications*. Totowa, N.J.: Humana Press 1993.

Using pGEMT-TS (Example 1) as template, the Thr (T) at position 299 of the wild-type glucose isomerase was mutated to Gln (Q) to generate glucose isomerase mutant MGI-T299Q by PCR amplification with site-directed primers 299QF and 299QR (Table 1) and universal primers T1 and T2 (Example 1).

Fragment T1QR was amplified using primer pair T1 and 299QR. Fragment QFT2 was amplified using primer pair 299QF and T2. The amplification condition was: 20 mM Tris-HCl (pH 8.8), 10 mM KCl, 10 mM (NH$_4$)$_2$SO$_4$, 2 mM MgSO$_4$, 0.1% Triton X-100, 50 µM dATP, 50 µM dTTP, 50 µM dCTP, 50 µM dGTP, 400 nM primer T1 and 400 nM primer 299QR or 400 nM primer T2 and 400 nM primer 299QF, 115 U Pfu DNA polymerase, 20 ng pGEMT-TS, and the total volume was adjusted to 50 µl with sterile distilled water. The PCR amplification program for the reaction was: 95° C., 3 min; then 35 cycles of 95° C., 50 sec, 52° C., 30 sec, 72° C., 3 min; and finally 72° C., 5 min. The PCR products, fragment T1QR and fragment QFT2, were separated on 1% agarose gel and recovered using QIAquick Gel Extraction Kit. The full-length glucose isomerase gene was then assembled on the following condition: 20 mM Tris-HCl (pH 8.8), 10 mM KCl, 10 mM (NH$_4$)$_2$SO$_4$, 2 mM MgSO$_4$, 0.1% Triton X-100, 50 µM dATP, 50 µM dTTP, 50 µM dCTP, 50 µM dGTP, 400 nM primer T1 and 400 nM primer T2, 1.5 U Pfu DNA polymerase, 20 ng fragment T1 QR and 20 ng fragment QFT2, and the total volume was adjusted to 50 µl with sterile distilled water. The PCR amplification program for the reaction was: 95° C., 3 min; then 35 cycles of 95° C., 50 sec, 52° C., 30 see, 72° C., 3 min; and finally 72° C., 5 min. The full-length mutant MGI-T299Q was separated on 1% agarose gel and recovered using QIAquick Gel Extraction Kit. Plasmid pGEMT-MGI-T299Q, generated after ligation of MGI-T299Q into vector pGEMT-Easy, was transformed into competent *E. coli* HB101 and the transformants were screened for glucose isomerase activity on 1% MacConkey plates containing 1% D-xylose and 50 mg/L ampicillin. Plasmid pGEMT-MGI-T299Q DNA was then isolated from the positive clones and sequenced. The amino acid sequence of MGI-T299Q is shown as Sequence 8 in the Sequence Listing and the specific activity thereof is shown in Table 2.

Example 6

Generation of Glucose Isomerase Mutant MGI-2 Containing Two Mutations

The site directed mutagenesis was done as described by Ho et al., *Gene* 77:51-59, 1989 and White et al., *PCR protocol: current methods and applications*. Totowa, N.J.: Humana Press 1993.

Fragments T1FR and AFT2 were amplified and recovered in accordance with Examples 2 and 3 respectively. Fragment FFAR was amplified using primer pair 139FF (Example 2) and 182AR (Example 3) on the following condition: 20 mM Tris-HCl (pH 8.8), 10 mM KCl, 10 mM (NH$_4$)$_2$SO$_4$, 2 mM MgSO$_4$, 0.1% Triton X-100, 50 µM dATP, 50 µM dTTP, 50 µM dCTP, 50 µM dGTP, 400 nM primer 139FF and 400 nM primer 182AR, 1.5 U Pfu DNA polymerase, 20 ng pGEMT-TS, and the total volume was adjusted to 50 µl with sterile distilled water. The PCR amplification program for the reaction was: 95° C., 3 min; then 35 cycles of 95° C., 50 sec, 52° C., 30 sec, 72° C., 3 min; and finally 72° C., 5 min. The PCR product, fragment FFAR, was separated on 1% agarose gel and recovered using QIAquick Gel Extraction Kit. The full length glucose isomerase gene was assembled at the following condition: 20 mm Tris-HCl (pH 8.8), 10 mM KCl, 10 mm (NH$_4$)$_2$SO$_4$, 2 mM MgSO$_4$, 0.1% Triton X-100, 50 µM dATP, 50 µM dTTP, 50 µM dCTP, 50 µM dGTP, 400 nM primer T1 and 400 nM primer T2, 1.5 U Pfu DNA polymerase, 20 ng fragment T1FR, 20 ng fragment FFAR, 20 ng fragment AFT2 and the total volume was adjusted to 50 µl with sterile distilled water. The PCR amplification program for the reaction was: 95° C., 3 min; then 35 cycles of 95° C., 50 sec, 52° C., 30 sec, 72° C., 3 min; and finally 72° C., 5 min. The full-length mutant MGI-2 was separated on 1% agarose gel and recovered using QIAquick Gel Extraction Kit. Plasmid pGEMT-MGI-2, generated after ligation of MGI-2 into vector pGEMT-Easy, was transformed into competent *E. coli* HB101 and the transformants were screened for glucose isomerase activity on 1% MacConkey plates containing 1% D-xylose and 50 mg/L ampicillin. Plasmid pGEMT-MGI-2 DNA was then isolated from the positive clones and sequenced. The sequence of the MGI-2 contains two mutations including W139F and R182A. The amino acid sequence of MGI-2 is shown as Sequence 9 in the Sequence Listing and the specific activity thereof is shown in Table 2.

Example 7

Generation of Glucose Isomerase Mutant MGI-3 Containing Three Mutations

The site directed mutagenesis was done as described by Ho et al., *Gene* 77:51-59, 1989 and White et al., *PCR protocol: current methods and applications*. Totowa, N.J.: Humana Press 1993.

Fragments T1FR, QFT2 and FFAR were amplified and recovered in accordance with Examples 2, 5 and 6 respectively. Fragment AFQR was amplified using primer pair 182AF (Example 3) and 299QR (Example 5) on the following condition: 20 mM Tris-HCl (pH 8.8), 10 mM KCl, 10 mM (NH$_4$)$_2$SO$_4$, 2 mM MgSO$_4$, 0.1% Triton X-100, 50 µM dATP, 50 µM dTTP, 50 µM dCTP, 50 dGTP, 400 nM primer 182AF and 400 nM primer 299QR, 1.5 U Pfu DNA polymerase, 20 ng pGEMT-TS, and the total volume was adjusted to 50 µl with sterile distilled water. The PCR amplification program for the reaction was: 95° C., 3 min; then 35 cycles of 95° C., 50 sec, 52° C., 30 sec, 72° C., 3 min; and finally 72° C., 5 min. The PCR product, fragment AFQR, was separated on 1% agarose gel and recovered using QIAquick Gel Extraction Kit. The full length glucose isomerase gene was assembled at the following condition: 20 mM Tris-HCl (pH 8.8), 10 mM KCl, 10 mM $(NH_4)_2SO_4$, 2 mM $MgSO_4$, 0.1% Triton X-100, 50 µM dATP, 50 µM dTTP, 50 µM dCTP, 50 µM dGTP, 400 nM primer T1 and 400 nM primer T2, 1.5 U Pfu DNA polymerase, 20 ng fragment T1FR, 20 ng fragment FFAR, 20 ng fragment AFQR and 20 ng fragment QFT2 and the total volume was adjusted to 50 µl with sterile distilled water. The PCR amplification program for the reaction was: 95° C., 3 min; then 35 cycles of 95° C., 50 sec, 52° C., 30 sec, 72° C., 3 min; and finally 72° C., 5 min. The full-length mutant MGI-3 was separated on 1% agarose gel and recovered using QIAquick Gel Extraction Kit. Plasmid pGEMT-MGI-3, generated after ligation of MGI-3 into vector pGEMT-Easy, was transformed into competent *E. coli* HB3101 and the transformants were screened for glucose isomerase activity on 1% MacConkey plates containing 1% D-xylose and 50 mg/L ampicillin. Plasmid pGEMT-MGI-3 DNA was then isolated from the positive clones and sequenced. The sequence of the MGI-3 contains three mutations including W139F, R182A and T299Q. The amino acid sequence of MGI-3 is shown as Sequence 10 in the Sequence Listing and the specific activity thereof is shown in Table 2.

Example 8

Generation of Glucose Isomerase Mutant MGI-4 Containing Four Mutations

The site directed mutagenesis was done as described by Ho et al., *Gene* 77:51-59, 1989 and White et al., *PCR protocol: current methods and applications*. Totowa, N.J.: Humana Press 1993.

Fragments T1FR, QFT2 and FEAR were amplified and recovered in accordance with Examples 2, 5 and 6 respectively. Fragment AFSR was amplified using primer pair 182AF (Example 3) and 187SR Example 4) on the following condition: 20 mM Tris-HCl (pH 8.8), 10 mM KCl, 10 mM $(NH_4)_2SO_4$, 2 mM $MgSO_4$, 0.1% Triton X-100, 50 µM dATP, 50 µM dTTP, 50 µM dCTP, 50 µM dGTP, 400 nM primer 182AF and 400 nM primer 187SR, 1.5 U Pfu DNA polymerase, 20 ng pGEMT-TS, and the total volume was adjusted to 50 µl with sterile distilled water. The PCR amplification program for the reaction was: 95° C., 3 min; then 35 cycles of 95° C., 50 sec, 52° C., 30 sec, 72° C., 3 min; and finally 72° C., 5 min. The PCR product, fragment AFSR, was separated on 1% agarose gel and recovered using QIAquick Gel Extraction Kit. Fragment SFQR was amplified using primers 187SF (Example 4) and 299QR (Example 5) at the following condition: 20 mM Tris-HCl (pH 8.8), 10 mM KCl, 10 mM $(NH_4)_2SO_4$, 2 mM $MgSO_4$, 0.1% Triton X-100, 50 µM dATP, 50 µM dTTP, 50 µM dCTP, 50 µM dGTP, 400 mM primer 187SF and 400 nM primer 299QR, 1.5 U Pfu DNA polymerase, 20 ng pGEMT-TS and the total volume was adjusted to 50 µl with sterile distilled water. The PCR amplification program for the reaction was: 95° C., 3 min; then 35 cycles of 95° C., 50 sec, 52° C., 30 sec, 72° C., 3 min; and finally 72° C., 5 min. The fragment SFQR was separated on 1% agarose gel and recovered using QIAquick Gel Extraction Kit. The full length glucose isomerase gene was assembled at the following condition: 20 mM Tris-HCl (pH 8.8), 10 mM KCl, 10 mM $(NH_4)_2SO_4$, 2 mM $MgSO_4$, 0.1% Triton X-100, 50 µM dATP, 50 µM dTTP, 50 µM dCTP, 50 µM dGTP, 400 mM primer T1 and 400 nM primer T2, 1.5 U Pfu DNA polymerase, 20 ng fragment T1FR, 20 ng fragment FFAR, 20 ng fragment AFSR, 20 ng fragment SFQR and 20 ng fragment QFT2 and the total volume was adjusted to 50 µl with sterile distilled water. The PCR amplification program for the reaction was: 95° C., 3 min; then 35 cycles of 95° C., 50 sec, 52° C., 30 sec, 72° C., 3 min; and finally 72° C., 5 min. The full-length mutant MGI-4 was separated on 1% agarose gel and recovered using QIAquick Gel Extraction Kit. Plasmid pGEMT-MGI-4, generated after ligation of MGI-4 into vector pGEMT-Easy, was transformed into competent *E. coli* HB101 and the transformants were screened for glucose isomerase activity on 1% MacConkey plates containing 1% D-xylose and 50 mg/L ampicillin. Plasmid pGEMT-MGI-4 DNA was then isolated from the positive clones and sequenced. The sequence of the MGI-4 contains four mutations including W139F, R182A, F187S and T299Q. The amino acid sequence of MGI-4 is shown as Sequence 11 in the Sequence Listing and the specific activity thereof is shown in Table 2.

Example 9

Saturated Mutagenesis of Position 139 of Four-Mutation Glucose Isomerase Mutant MGI-4

The site directed mutagenesis was done as described by Ho et al., *Gene* 77:51-59, 1989 and White et al., *PCR protocol: current methods and applications*. Totowa, N.J.: Humana Press 1993.

Using pGEMT-MGI-4 Example 8) as template, the Phe (P) at position 139 of the glucose isomerase mutant MGI-4 was mutated to Ser (S) to generate glucose isomerase mutant MGI4-F139S by PCR amplification with site-directed primers 139SF and 139SR (Table 1) and universal primers T1 and T2 (Example 1).

Fragment T1SR was amplified using primer pair T1 and 139SR. Fragment SFT2 was amplified using primer pair 139SF and T2. The amplification condition was: 20 mM Tris-HCl (pH 8.8), 10 mM KCl, 10 mM $(NH_4)_2SO_4$, 2 mM $MgSO_4$, 0.1% Triton X-100, 50 µM dATP, 50 µM dTTP, 50 µM dCTP, 50 µM dGTP, 400 nM primer T1 and 400 nM primer 139SR or 400 nM primer T2 and 400 nM primer 1395, 1.5 U Pfu DNA polymerase (Promega, USA), 20 ng pGEMT-MGI-4, and the total volume was adjusted to 50 µl with sterile distilled water. The PCR amplification program for the reaction was: 95° C., then 35 cycles of 95° C., 50 sec, 52° C., 30 sec, 72° C., 3 min; and finally 72° C., 5 min. The PCR products, fragment T1SR and fragment SFT2, were separated on 1% agarose gel and recovered using QIAquick Gel Extraction Kit (QIAGEN, German). The full-length glucose isomerase gene was then assembled on the following condition: 20 mM Tris-HCl (pH 8.8), 10 mM KCl, 10 mM $(NH_4)_2SO_4$, 2 mM $MgSO_4$, 0.1% Triton X-100, 50 µM dATP, 50 µM dTTP, 50 µM dCTP, 50 µM dGTP, 400 nM primer T1 and 400 no primer T2, 1.5 U Pfu DNA polymerase, 20 ng fragment T1SR and 20 ng fragment SFT2, and the total volume was adjusted to 50 µl with sterile distilled water. The PCR amplification program for the reaction was: 95° C., 3 min; then 35 cycles of 95° C., 50 sec, 52° C., 30 sec, 72° C., 3 min; and finally 72° C., 0, 5 min. The full-length mutant MGI4-F139S was separated on 1% agarose gel and recovered using QIAquick Gel Extraction Kit. Plasmid pGEMT-MGI4-F139S, generated after ligation of MGI4-F139S into vector pGEMT-Easy, was transformed into competent *E. coli* HB101 and the transformants were screened for glucose isomerase activity on 1% MacConkey plates containing 1% D-xylose and 50 mg/L ampicillin. Plasmid pGEMT-MGI4-F139S DNA was then isolated from the positive clones and sequenced. The sequence of the MGI4-F139S contains four mutations including F139S, R182A, F187S and T299Q. The amino acid sequence of MGI4-F139S is shown as Sequence 12 in the Sequence Listing and the specific activity thereof is shown in Table 2.

Mutants MGI4-F139K, MGI4-F139C, MGI4-F139I, MGI4-F139T, MGI4-F139N and MGI4-F139D were constructed with similar procedures. The primers used are shown in Table 1. The amino acid sequences are shown as Sequences 13-18 in the Sequence Listing and the specific activities thereof are shown in Table 2.

Example 10

Saturated Mutagenesis of Position 182 of Four-Mutation Glucose Isomerase Mutant MGI-4

The site directed mutagenesis was done as described by Ho et al., *Gene* 77:51-59, 1989 and White et al., *PCR protocol: current methods and applications*. Totowa, N.J.: Humana Press 1993.

Using pGEMT-MGI-4 (Example 8) as template, the Ala (A) at position 182 of the glucose isomerase mutant MGI-4 was mutated to Pro (P) to generate glucose isomerase mutant MGI4-A182P by PCR amplification with site-directed primers 182 PF and 182PR (Table 1) and universal primers T1 and T2 (Example 1).

Fragment T1PR was amplified using primer pair T1 and 182PR. Fragment PFT2 was amplified using primer pair 182PF and T2. The amplification condition was: 20 mM Tris-HCl (pH 8.8), 10 mM KCl, 10 mM $(NH_4)_2SO_4$, 2 mM $MgSO_4$, 0.1% Triton X-100, 50 µM dATP, 50 µM dTTP, 50 µM dCTP, 50 µM dGTP, 400 nM primer T1 and 400 nM primer 182PR or 400 nM primer T2 and 400 nM primer 182 PF, 1.5 U Pfu DNA polymerase, 20 ng pGEMT-MGI-4, and the total volume was adjusted to 50 µl with sterile distilled water. The PCR amplification program for the reaction was: 95° C., 3 min; then 35 cycles of 95° C., 50 sec, 52° C., 30 sec, 72° C., 3 min; and finally 72° C., 5 min. The PCR products, fragment T1PR and fragment PFT2, were separated on 1% agarose gel and recovered using QIAquick Gel Extraction Kit. The full-length glucose isomerase gene was then assembled on the following condition: 20 mM Tris-HCl (pH 8.8), 10 mM KCl, 10 mM $(NH_4)_2SO_4$, 2 mM $MgSO_4$, 0.1% Triton X-100, 50 µM dATP, 50 µM dTTP, 50 µM dCTP, 50 µM dGTP, 400 nM primer T1 and 400 nM primer T2, 1.5 U Pfu DNA polymerase, 20 ng fragment T1PR and 20 ng fragment PFT2, and the total volume was adjusted to 50 µl with sterile distilled water. The PCR amplification program for the reaction was: 95° C., 3 min; then 35 cycles of 95° C., 50 sec 52° C., 30 sec, 72° C., 3 min; and finally 72° C., 5 min. The full-length mutant MGI4-A182P was separated on 1% agarose gel and recovered using QIAquick Gel Extraction Kit. Plasmid pGEMT-MGI4-A182P, generated after ligation of MGI4-A182P into vector pGEMT-Easy, was transformed into competent *E. coli* HB101 and the transformants were screened for glucose isomerase activity on 1% MacConkey plates containing 1% D-xylose and 50 mg/L ampicillin. Plasmid pGEMT-MGI4-A182P DNA was then isolated from the positive clones and sequenced. The sequence of the MGI4-A182P contains four mutations including W139F, A182P, F187S and T299Q. The amino acid sequence of MGI4-A182P is shown as Sequence 19 in the Sequence Listing and the specific activity thereof is shown in Table 2.

Mutants MGI4-A182S, MGI4-A182I, MGI4-A182T and MGI4-A182V were constructed with similar procedures. The primers used are shown in Table 1. The amino acid sequences are shown as Sequences 20-23 in the Sequence Listing and the specific activities thereof are shown in Table 2.

Example 11

Saturated Mutagenesis of Position 187 of Four-Mutation Glucose Isomerase Mutant MGI-4

The site directed mutagenesis was done as described by Ho et al., *Gene* 77:51-59, 1989 and White et al., *PCR protocol: current methods and applications*. Totowa, N.J.: Humana Press 1993.

Using pGEMT-MGI-4 (Example 8) as template, the Ser (S) at position 187 of the glucose isomerase mutant MGI-4 was mutated to Gly (G) to generate glucose isomerase mutant MGI-4-S187G by PCR amplification with site-directed primers 187GF and 187GR (Table 1) and universal primers T1 and T2 (Example 1).

Fragment T1GR was amplified using primer pair T1 and 187GR. Fragment GFT2 was amplified using primer pair 187GF and T2. The amplification condition was: 20 mM Tris-HCl (pH 8.8), 10 mM KCl, 10 mM $(NH_4)_2SO_4$, 2 mM $MgSO_4$, 0.1% Triton X-100, 50 µM dATP, 50 µM dTTP, 50 µM dCTP, 50 µM dGTP, 400 nM primer T1 and 400 nM primer 187GR or 400 nM primer T2 and 400 nM primer 187GF, 1.5 U Pfu DNA polymerase, 20 ng pGEMT-MGI-4, and the total volume was adjusted to 50 µl with sterile distilled water. The PCR amplification program for the reaction was: 95° C., 3 min; then 35 cycles of 95° C., 50 sec, 52° C., 30 sec, 72° C., 3 min; and finally 72° C., 5 min. The PCR products, fragment T1GR and fragment GFT2, were separated on 1% agarose gel and recovered using QIAquick Gel Extraction Kit. The full-length glucose isomerase gene was then assembled on the following condition: 20 mM Tris-HCl (pH 8.8), 10 mM KCl, 10 mM $(NH_4)_2SO_4$, 2 mM $MgSO_4$, 0.1% Triton X-100, 50 µM dATP, 50 µM dTTP, 50 µM dCTP, 50 µM dGTP, 400 nM primer T1 and 400 nM primer T2, 1.5 U Pfu DNA polymerase, 20 ng fragment T1GR and 20 ng fragment GFT2, and the total volume was adjusted to 50 µl with sterile distilled water. The PCR amplification program for the reaction was: 95° C., 3 min; then 35 cycles of 95° C., 50 sec, 52° C., 30 sec, 72° C., 3 min; and finally 72° C., 5 min. The full-length mutant MGI4-S187G was separated on 1% agarose gel and recovered using QIAquick Gel Extraction Kit. Plasmid pGEMT-MGI4-S187G, generated after ligation of MGI4-S187G into vector pGEMT-Easy, was transformed into competent *E. coli* HB101 and the transformants were screened for glucose isomerase activity on 1% MacConkey plates containing 1% D-xylose and 50 mg/L ampicillin. Plasmid pGEMT-MGI4-S187G DNA was then isolated from the positive clones and sequenced. The sequence of the MGI4-S187G contains four mutations including W139F, R182A, S187G and T299Q The amino acid sequence of MGI4-S187G is shown as Sequence 24 in the Sequence Listing and the specific activity thereof is shown in Table 2.

Mutants MGI4-S187A and MGI4-S187P were constructed with similar procedures. The primers used are shown in Table 1. The amino acid sequences are shown as Sequences 25-26 in the Sequence Listing and the specific activities thereof are shown in Table 2.

Example 12

Saturated Mutagenesis of Position 299 of Four-Mutation Glucose Isomerase Mutant MGI-4

The site directed mutagenesis was done as described by Ho et al., *Gene* 77:51-59, 1989 and White et al., *PCR protocol: current methods and applications*. Totowa, N.J.: Humana Press 1993.

Using pGEMT-MGI-4 (Example 8) as template, the Gln (Q) at position 299 of the glucose isomerase mutant MGI-4 was mutated to Ile (I) to generate glucose isomerase mutant MGI4-Q299I by PCR amplification with site-directed primers 299IF and 299IR (Table 1) and universal primers T1 and T2 (Example 1).

Fragment T1IR was amplified using primer pair T1 and 299IR. Fragment IFT2 was amplified using primer pair 299IF and T2. The amplification condition was: 20 M Tris-HCl (pH 8.8), 10 mM KCl, 10 mM $(NH_4)_2SO_4$, 2 mM $MgSO_4$, 0.1% Triton X-100, 50 µM dATP, 50 µM dTTP, 50 µM dCTP, 50 µM dGTP, 400 nM primer T1 and 400 nM primer 299IR or 400 nM primer T2 and 400 nM primer 299IF, 1.5 U Pfu DNA polymerase, 20 ng pGEMT-MGI-4, and the total volume was adjusted to 50 µl with sterile distilled water. The PCR amplification program for the reaction was: 95° C., 3 min; then 35 cycles of 95° C., 50 sec, 52° C., 30 sec, 72° C., 3 min; and finally 72° C., 5 min. The PCR products, fragment T1IR and fragment IFT2, were separated on 1% agarose gel and recovered using QIAquick Gel Extraction Kit. The full-length glucose isomerase gene was then assembled on the following condition: 20 mM Tris-HCl (pH 8.8), 10 mM KCl, 10 mM $(NH_4)_2SO_4$, 2 mM $MgSO_4$, 0.1% Triton X-100, 50 µM dATP, 50 µM dTTP, 50 µM dCTP, 50 µM dGTP, 400 nM primer T1 and 400 nM primer T2, 1.5 U Pfu DNA polymerase, 20 ng fragment T1IR and 20 ng fragment IFT2, and the total volume was adjusted to 50 µl with sterile distilled water. The PCR amplification program for the reaction was: 95° C., 3 min; then 35 cycles of 95° C., 50 sec 52° C., 30 sec, 72° C., 3 min. and finally 72° C., 5 min. The full-length mutant MGI4-Q299I was separated on 1% agarose gel and recovered using QIAquick Gel Extraction Kit. Plasmid pGEMT-MGI4-Q299I, generated after ligation of MGI4-Q299I into vector pGEMT-Easy, was transformed into competent *E. coli* HB101 and the transformants were screened for glucose isomerase activity on 1% MacConkey plates containing 1% D-xylose and 50 mg/L ampicillin. Plasmid pGEMT-MGI4-Q299I DNA was then isolated from the positive clones and sequenced. The sequence of the MGI4-Q299I contains four mutations including W139F, R182A, F187S and Q299I. The amino acid sequence of MGI4-Q299I is shown as Sequence 27 in the Sequence Listing and the specific activity thereof is shown in Table 2.

Mutants MGI4-Q299Y, MGI4-Q299C, MGI4-Q299M and MGI4-Q299E were constructed with similar procedures. The primers used are shown in Table 1. The amino acid sequences are shown as Sequences 28-31 in the Sequence Listing and the specific activities thereof are shown in Table 2.

Example 13

Generation of Five-Mutation Glucose Isomerase Mutants MGI4-F87L, MGI4-F87M, MGI4-V217R, MGI4-D260E and MGI4-F276G

The site directed mutagenesis was done as described by Ho et al., *Gene* 77:51-59, 1989 and White et al., *PCR protocol: current methods and applications*, Totowa, N.J.: Humana Press 1993.

Using pGEMT-MGI-4 (Example 8) as template, the Phe (F) at position 87 of the MGI-4 was mutated to Leu (L) to generate glucose isomerase mutant MGI4-F87L by PCR amplification with site-directed primers 87LF and 87LR (Table 1) and universal primers T1 and T2 (Example 1).

Fragment T1LR was amplified using primer pair T1 and 87LR. Fragment LFT2 was amplified using primer pair 87LF and T2. The amplification condition was: 20 mM Tris-HCl (pH 8.8), 10 mM KCl, 10 mM $(NH_4)_2SO_4$, 2 mM $MgSO_4$, 0.1% Triton X-100, 50 µM dATP, 50 µM dTTP, 50 µM dCTP, 50 µM dGTP, 400 nM primer T1 and 400 nM primer 87LR or 400 nM primer T2 and 400 nM primer 87LF, 1.5 U Pfu DNA polymerase (Promega, USA), 20 ng pGEMT-MGI-4, and the total volume was adjusted to 50 µl with sterile distilled water. The PCR amplification program for the reaction was: 95° C., 3 min; then 35 cycles of 95° C., 50 sec, 52° C., 30 sec, 72° C., 3 min; and finally 72° C., 5 min. The PCR products, fragment T1LR and fragment LFT2, were separated on 1% agarose gel and recovered using QIAquick Gel Extraction Kit (QIAGEN, German). The full-length glucose isomerase gene was then assembled on the following condition: 20 mM Tris-HCl (pH 8.8), 10 mM KCl, 10 mM $(NH_4)_2SO_4$, 2 mM $MgSO_4$, 0.1% Triton X-100, 50 µM dATP, 50 µA dTTP, 50 µM dCTP, 50 µM dGTP, 400 mM primer T1 and 400 nM primer T2, 1.5 U Pfu DNA polymerase, 20 ng fragment T1LR and 20 ng fragment LFT2, and the total volume was adjusted to 50 µl with sterile distilled water. The PCR amplification program for the reaction was: 95° C., 3 min; then 35 cycles of 95° C., 50 sec, 52° C., 30 sec, 72° C., 3 min; and finally 72° C., 5 min. The full-length mutant MGI4-F87L was separated on 1% agarose gel and recovered using QIAquick Gel Extraction Kit. Plasmid pGEMT-MGI4-F87L, generated after ligation of MGI4-F87L into vector pGEMT-Easy, was transformed into competent *E. coli* HB101 and the transformants were screened for glucose isomerase activity on 1% MacConkey plates containing 1% D-xylose and 50 mg/L ampicillin. Plasmid pGEMT-MGI4-F87L DNA was then isolated from the positive clones and sequenced. The sequence of the MGI4-F87L contains five mutations including F87L, W139F, R182A, F187S and T299Q. The amino acid sequence of MGI4-F87L is shown as Sequence 32 in the Sequence Listing and the specific activity thereof is shown in Table 2.

Mutant MGI4-F87M was constructed with similar procedures. The primers used are shown in Table 1. The sequence of the mutant MGI4-F87M contains five mutations including F87M, W139F, R182A, F187S and T299Q. The amino acid sequence is shown as Sequence 33 in the Sequence Listing and the specific activity thereof is shown in Table 2. Mutant MGI4-V217R was constructed with similar procedures. The primers used are shown in Table 1. The sequence of the mutant MGI4-V217R contains five mutations including W139F, R182A, F187S, V217R and T299Q. The amino acid sequence of MGI4-V217R is shown as Sequence 34 in the Sequence Listing and the specific activity thereof is shown in Table 2. Mutant MGI4-D260E was constructed with similar procedures. The primers used are shown in Table 1. The sequence of the mutant contains five mutations including W139F, R192A, F187S, D260E and T299Q. The amino acid sequence of MGI4-D260E is shown as Sequence 35 in the Sequence Listing and the specific activity thereof is shown in Table 2. Mutant MGI4-F276G was constructed with similar procedures. The primers used are shown in Table 1. The sequence of the mutant contains five mutations including W139F, R182A, F117S, F276G and T299Q. The amino acid sequence of MGI4-F276G is shown as Sequence 36 in the Sequence Listing and the specific activity thereof is shown in Table 2.

15

Example 14

Generation of Six-Mutation Glucose Isomerase Mutants MGI4-24 and MGI4-25

The site directed mutagenesis was done as described by Ho et al., *Gene* 77:51-59, 1989 and White et al., *PCR protocol: current methods and applications*. Totowa, N.J.: Humana Press 1993.

Fragment T1LR was amplified and recovered as in Example 13. Fragment LFAR was amplified using primer pair 87LF and 260AR (Table 1). The amplification condition was: 20 mM Tris-HCl (pH 8.8), 10 mM KCl, 10 mM $(NH_4)_2SO_4$, 2 mM $MgSO_4$, 0.1% Triton X-100, 50 µM dATP, 50 µM dTTP, 50 µM dCTP, 50 µM dGTP, 400 nM primer 87LF and 400 nM primer 260AR, 1.5 U Pfu DNA polymerase, 20 ng pGEMT-MGI-4, and the total volume was adjusted to 50 µl with sterile distilled water. The PCR amplification program for the reaction was: 95° C., 3 min; then 35 cycles of 95° C., 50 sec, 52° C., 30 sec, 72° C., 3 min; and finally 72° C., 5 min. The PCR product, fragment LFAR, was separated on 1% agarose gel and recovered using QIAquick Gel Extraction Kit. Fragment AFT2 was amplified using primer pair 260AF and T2 (Table 1) and recovered. The amplification condition was: 20 mM Tris-HCl (pH 8.8), 10 mM KCl, 10 mM $(NH_4)_2SO_4$, 2 mM $MgSO_4$, 0.1% Triton X-100, 50 µM dATP, 50 µM dTTP, 50 µM dCTP, 50 µM dGTP, 400 mM primer 260AF and 400 nM primer T2, 1.5 U Pfu DNA polymerase, 20 ng pGEMT-MGI-4, and the total volume was adjusted to 50 µl with sterile distilled water. The PCR amplification program for the reaction was: 95° C., 3 min; then 35 cycles of 95° C., 50 sec, 52° C., 30 sec, 72° C., 3 min; and finally 72° C., 5 min. The PCR product, fragment AFT2 was separated on 1% agarose gel and recovered using QIAquick Gel Extraction Kit. The full-length glucose isomerase gene was then assembled on the following condition: 20 mM Tris-HCl (pH 8.8), 10 mM KCl, 10 mM)$_2SO_4$, 2 mM $MgSO_4$, 0.1% Triton X-100, 50 W dATP, 50 µM dTTP, 50 µM dCTP, 50 µM dGTP, 400 nM primer T1 and 400 nM primer T2, 1.5 U Pfu DNA polymerase, 20 ng fragment T1LR, 20 ng fragment LFAR and 20 ng fragment AFT2, and the total volume was adjusted to 50 µl with sterile distilled water. The PCR amplification program for the reaction was: 95° C., 3 min; then 35 cycles of 95° C., 50 sec, 52° C., 30 sec, 72° C., 3 min; and finally 72° C., 5 min. The full-length mutant MGI4-24 was separated on 1% agarose gel and recovered using QIAquick Gel Extraction Kit. Plasmid pGEMT-MGI4-24, generated after ligation of MGI4-24 into vector pGEMT-Easy, was transformed into competent *E. coli* HB101 and the transformants were screened for glucose isomerase activity on 1% MacConkey plates containing 1% D-xylose and 50 mg/L ampicillin. Plasmid pGEMT-MGI4-24 DNA was then isolated from the positive clones and sequenced. The sequence of the MGI4-24 contains six mutations including F87L, W139F, R182A, F187S, T299Q and D260A, The amino acid sequence of MGI4-24 is shown as Sequence 37 in the Sequence Listing and the specific activity thereof is shown in Table 2.

Mutant MGI4-25 was constructed with similar procedures. The primer pairs used were T1 and 87LR, 87LF and 276TR, 276TF and T2 (Table 1). The sequence of the mutant contains six mutations including F87L, W139F, R182A, F187S, T299Q and F276T. The amino acid sequence is shown as Sequence 38 in the Sequence Listing and the specific activity thereof is shown in Table 2.

Example 15

Generation of Seven-Mutation Glucose Isomerase Mutants MGI4-34 and MGI4-35

The site directed mutagenesis was done as described by Ho et al., *Gene* 77:51-59, 1989 and White et al., *PCR protocol: current methods and applications*. Totowa, N.J.: Humana Press 1993.

Fragment T1LR was amplified and recovered as in Example 13. Fragment LFGR was amplified using primer pair 87LF and 217GR (Table 1). The amplification condition was: 20 mM Tris-HCl (pH 8.8), 10 mM KCl, 10 mM $(NH_4)_2SO_4$, 2 mM $MgSO_4$, 0.1% Triton X-100, 50 µM dATP, 50 µM dTTP, 50 µM dCTP, 50 µM dGTP, 400 nM primer 87LF and 400 nM primer 217GR, 1.5 U Pfu DNA polymerase, 20 ng pGEMT-MGI-4, and the total volume was adjusted to 50 µl with sterile distilled water. The PCR amplification program for the reaction was: 95° C., 3 min; then 35 cycles of 95° C., 50 sec, 52° C., 30 sec, 72° C., 3 min; and finally 72° C., 5 min. The PCR product, fragment LFGR, was separated on 1% agarose gel and recovered using QIAquick Gel Extraction Kit. Fragment GFTR was amplified using primer pair 217GF and 276TR (Table 1) and recovered. The amplification condition was: 20 mM Tris-HCl (pH 8.8), 10 mM KCl, 10 mM $(NH_4)_2SO_4$, 2 mM $MgSO_4$, 0.1% Triton X-100, 50 µM dATP, 50 µM dTTP, 50 µM dCTP, 50 µM dGTP, 400 nM primer 217GF and 400 nM primer 276TR, 1.5 U Pfu DNA polymerase, 20 ng pGEMT-MGI-4, and the total volume was adjusted to 50 µl with sterile distilled water. The PCR amplification program for the reaction was: 95° C., 3 min; then 35 cycles of 95° C., 50 sec, 52° C., 30 sec, 72° C., 3 min; and finally 72° C., 5 min. The PCR product, fragment GFTR was separated on 1% agarose gel and recovered using QIAquick Gel Extraction Kit. Fragment TFT2 was amplified using primer pair 276TF and T2 (Table 1) and recovered. The amplification condition was: 20 mM Tris-HCl (pH 8.8), 10 mM KCl, 10 mM $(NH_4)_2SO_4$, 2 mM $MgSO_4$, 0.1% Triton X-100, 50 µM dATP, 50 µM dTTP, 50 µM dCTP, 50 µM dGTP, 400 nM primer 276TF and 400 nM primer T2, 1.5 U Pfu DNA polymerase, 20 ng pGEMT-MGI-4, and the total volume was adjusted to 50 µl with sterile distilled water. The PCR amplification program for the reaction was: 95° C., 3 min; then 35 cycles of 95° C., 50 sec, 52° C., 30 sec, 72° C., 3 min; and finally 72° C., 5 min. The PCR product, fragment TFT2 was separated on 1% agarose gel and recovered using QIAquick Gel Extraction Kit. The full-length glucose isomerase gene was then assembled on the following condition: 20 mM Tris-HCl (pH 8.8), 10 mM KCl, 10 mM $(NH_4)_2SO_4$, 2 mM $MgSO_4$, 0.1% Triton X-100, 50 µM dATP, 50 µM dTTP, 50 µM dCTP, 50 µM dGTP, 400 nM primer T1 and 400 nM primer T2, 1.5 U Pfu DNA polymerase, 20 ng fragment T1LR, 20 ng fragment LFAR, 20 ng fragment GFTR and 20 ng fragment TFT2, and the total volume was adjusted to 50 µl with sterile distilled water. The PCR amplification program for the reaction was: 95° C., 3 min; then 35 cycles of 95° C., 50 sec. 52° C., 30 sec. 72° C., 3 min; and finally 72° C., 5 min. The fall-length mutant MGI4-34 was separated on 1% agarose gel and recovered using QIAquick Gel Extraction Kit. Plasmid pGEMT-MGI4-34, generated after ligation of MGI4-34 into vector pGEMT-Easy, was transformed into competent *E. coli* HB101 and the transformants were screened for glucose isomerase activity on 1% MacConkey plates containing 1% D-xylose and 50 mg/L ampicillin. Plasmid pGEMT-MGI4-34 DNA was then isolated from the positive clones and sequenced. The sequence of the MGI4-34 contains seven mutations including F87L, W139F, R182A, F187S, T299Q, V217G and F276T. The amino acid sequence of MGI4-34 is shown as Sequence 39 in the Sequence Listing and the specific activity thereof is shown in Table 2.

Mutant MGI4-35 with seven-mutation was constructed with similar procedures. The primer pairs used were T1 and 87LR, 87LF and 217GR, 217GF and 260AR, 260AF and T2 (Table 1). The sequence of the mutant contains seven mutations including F87L, W139F, R182A, F187S, T299Q, V217G and D260A. The amino acid sequence is shown as Sequence 40 in the Sequence Listing and the specific activity thereof is shown in Table 2.

TABLE 1

The Primers Used for Amplification of Wild-type Glucose Isomerase and the Mutants in Examples 1-15.

| Product | Primer Pair |
| --- | --- |
| Wild-type | T1: 5' AGCCTAGGTTAATTAACTTTAAGAAGGAGATATACATAT GAATAAATATTTTGAGA 3'<br>T2: 5' ATAAGCTCAGCGGCGCGCCTTATTCTGCAAACAAATAC 3' |
| Mutant MGI-W139F | 139FF: 5' AAAAGTTTTGTTTGGTACCGCAAATCTTTTCTC 3'<br>139FR: 5' TTGCGGTACCAAACAAAACTTTTGTCTTGCTGG 3' |
| Mutant MGI4-F139S | 139SF: 5' AAGTTTTGAGCGGTACCGCAAATCTTTTCT 3'<br>139SR: 5' TGCGGTACCGCTCAAAACTTTTGTCTTGCT 3' |
| Mutant MGI4-F139K | 139KF: 5' AAGTTTTGAAAGGTACCGCAAATCTTTTCT 3'<br>139KR: 5' TGCGGTACCTTTCAAAACTTTTGTCTTGCT 3' |
| Mutant MGI4-F139C | 139CF: 5' AAGTTTTGTGCGGTACCGCAAATCTTTTCT 3'<br>139CR: 5' TGCGGTACCGCACAAAACTTTTGTCTTGCT 3' |
| Mutant MGI4-F139I | 139IF: 5' AAGTTTTGATTGGTACCGCAAATCTTTTCT 3'<br>139IR: 5' TGCGGTACCAATCAAAACTTTTGTCTTGCT 3' |
| Mutant MGI4-F139T | 139TF: 5' AAGTTTTGACAGGTACCGCAAATCTTTTCT 3'<br>139TR: 5' TGCGGTACCTGTCAAAACTTTTGTCTTGCT 3 |
| Mutant MGI4-F139N | 139NF: 5' AAGTTTTGAACGGTACCGCAAATCTTTTCT 3'<br>139NR: 5' TGCGGTACCGTTCAAAACTTTTGTCTTGCT 3' |
| Mutant MGI4-F139D | 139DF: 5' AAGTTTTGGATGGTACCGCAAATCTTTTCT 3'<br>139DR: 5' TGCGGTACCATCCAAAACTTTTGTCTTGCT 3' |
| Mutant MGI-R182A | 182AF: 5' GGAGCTTGGCGCGGAAAACTACGTATTTTGGGG 3'<br>182AR: 5' CGTAGTTTTCCGCGCCAAGCTCCTTAGTAATCT 3' |
| Mutant MGI4-A182P | 182PF: 5' AGCTTGGCCCGGAAAACTACGTATTTTGGG 3'<br>182PR: 5' GTAGTTTTCCGGGCCAAGCTCCTTAGTAAT 3' |
| Mutant MGI4-A182S | 182SF: 5' AGCTTGGCTCAGAAAACTACGTATTTTGGG 3'<br>182SR: 5' GTAGTTTTCTGAGCCAAGCTCCTTAGTAAT 3' |
| Mutant MGI4-A182I | 182IF: 5' AGCTTGGCATTGAAAACTACGTATTTTGGG 3'<br>182IR: 5' GTAGTTTTCAATGCCAAGCTCCTTAGTAAT 3' |
| Mutant MGI4-A182T | 182TF: 5' AGCTTGGCACAGAAAACTACGTATTTTGGG 3'<br>182TR: 5' GTAGTTTTCTGTGCCAAGCTCCTTAGTAAT 3' |
| Mutant MGI4-A182V | 182VF: 5' AGCTTGGCGTGGAAAACTACGTATTTTGGG 3'<br>182VR: 5' GTAGTTTTCCACGCCAAGCTCCTTAGTAAT 3' |
| Mutant MGI-F187S | 187SF: 5' ACTACGTAAGCTGGGGTGGAAGAGAAGGGT 3'<br>187SR: 5' CCACCCCAGCTTACGTAGTTTTCGCGGCCA 3' |
| Mutant MGI4-S187G | 187GF: 5' ACTACGTAGGCTGGGGTGGAAGAGAAGGGT 3'<br>187GR: 5' CCACCCCAGCCTACGTAGTTTTCGCGGCCA 3' |
| Mutant MGI4-S187A | 187AF: 5' ACTACGTAGCGTGGGGTGGAAGAGAAGGGT 3'<br>187AR: 5' CCACCCCACGCTACGTAGTTTTCGCGGCCA 3' |
| Mutant MGI4-S187P | 187PF: 5' ACTACGTACCGTGGGGTGGAAGAGAAGGGT 3'<br>187PR: 5' CCACCCCACGGTACGTAGTTTTCGCGGCCA 3' |
| Mutant MGI-T299Q | 299QF: 5' TGACGCAAATCAAGGCGACATGCTTTGGGATG 3'<br>299QR: 5' GCATGTCGCCTTGATTTGCGTCGATTGATCCTA 3' |
| Mutant MGI4-Q299I | 299IF: 5' GACGCAAATATTGGCGACATGCTTTTAGGAT 3'<br>299IR: 5' CATGTCGCCAATATTTGCGTCGATTGATCCT 3' |
| Mutant MGI4-Q299Y | 299YF: 5' GACGCAAATTATGGCGACATGCTTTTAGGAT 3'<br>299YR: 5' CATGTCGCCATAATTTGCGTCGATTGATCCT 3' |

TABLE 1-continued

The Primers Used for Amplification of Wild-type
Glucose Isomerase and the Mutants in Examples 1-15.

| Product | Primer Pair |
|---|---|
| Mutant MGI4-Q299C | 299CF: 5' GACGCAAATTGCGGCGACATGCTTTTAGGAT 3'<br>299CR: 5' CATGTCGCCGCAATTTGCGTCGATTGATCCT 3' |
| Mutant MGI4-Q299M | 299MF: 5' GACGCAAATATGGGCGACATGCTTTTAGGAT 3'<br>299MR: 5' CATGTCGCCCATATTTGCGTCGATTGATCCT 3' |
| Mutant MGI4-Q299E | 299EF: 5' GACGCAAATGAAGGCGACATGCTTTTAGGAT 3'<br>299ER: 5' CATGTCGCCTTCATTTGCGTCGATTGATCCT 3' |
| Mutant MGI4-F87L | 87LF: 5' GAAGCAGCACTGGAGTTTTTTGATAAGATAA 3'<br>87LR: 5' AAAAACTCCAGTGCTGCTTCTACCCTTGCTTTC 3' |
| Mutant MGI4-F87M | 87MF: 5' GAAGCAGCAATGGAGTTTTTTGATAAGATAA 3'<br>87MR: 5' AAAAACTCCATTGCTGCTTCTACCCTTGCTTTC 3' |
| Mutant MGI4-V217R | 217RF: 5' ACATGGCTCGCGACTATGCAAAGGAAATCG 3'<br>217RR: 5' GCATAGTCGCGAGCCATGTGCAAAAATCTT 3' |
| Mutant MGI4-V217G | 217GF: 5' ACATGGCTGGCGACTATGCAAAGGAAATCG 3'<br>217GR: 5' GCATAGTCGCCAGCCATGTGCAAAAATCTT 3' |
| Mutant MGI4-D260E | 260EF: 5' ACGACCTTGAAAAATATTTCAAAGTAAATA 3'<br>260ER: 5' AAATATTTTTCAAGGTCGTATTTTCTCAAG 3' |
| Mutant MGI4-D260A | 260AF: 5' ACGACCTTGCGAAATATTTCAAAGTAAATA 3'<br>260AR: 5' AAATATTTCGCAAGGTCGTATTTTCTCAAG 3' |
| Mutant MGI4-F276G | 276GF: 5' ACATTGGCAGGCCACGACTTCCAACATGAGC 3'<br>276GR: 5' GAAGTCGTGGCCTGCCAATGTCGCATGGTTT 3' |
| Mutant MGI4-F276T | 276TF: 5' ACATTGGCAACCCACGACTTCCAACATGAGC 3'<br>276TR: 5' GAAGTCGTGGGTTGCCAATGTCGCATGGTTT 3' |

Example 16

Isolation and Purification of Wild-Type Glucose Isomerase

The isolation and purification of wild-type glucose isomerase were carried out in accordance with Lee et al., *Journal of General Microbiology*, 139:1227-1234, 1993.

Plasmid pGEMT-TS transformed *E. coli* HB101 cells were incubated on MacConkey plate containing 1% D-xylose and 50 mg/L ampicillin at 37° C. for 36 hours. A single colony from the plate was inoculated and cultivated in 5 ml LB supplemented with 50 mg/L ampicillin for 16 hours. The bacterial cells were pelleted, resuspended in 1 ml mM sodium phosphate buffer (pH 6.5), added $CoCl_2$ and $MgCl_2$ to final concentrations of 250 µM and 5 mM respectively, disrupted using ultrasonication and centrifuged at 17,800 g for 15 min at 10° C. to collect the supernatant as crude protein. The crude protein was heated at 80° C. for 10 min and centrifuged at 17,800 g for 15 min at 10° C. to remove the precipitate. The resultant partially purified glucose isomerase was used in the subsequent assays.

Example 17

Isolation and Purification of Glucose Isomerase Mutants

The isolation and purification of glucose isomerase mutant MGI4-35 were carried out as described in Example 16, except the plasmid used was pGEMT-MGI4-35. Other glucose isomerase mutants were also isolated and purified as described in Example 16.

Example 18

Activity Assay of Wild-Type Glucose Isomerase

Stock substrate solution A containing 1.0 M D-xylose, 20 mM sodium phosphate buffer (pH6.5), 250 µM $CoCl_2$ (final concentration) and 5 mM $MgCl_2$ (final concentration) was adjusted to pH 6.5. Ninety µl of the stock substrate solution A were mixed with 10 µl of the glucose isomerase prepared as described in Example 16, incubated at 80° C. for 10 min and quenched on ice immediately. The D-xylulose formed was measured by the cysteine-carbazole method (Dische et al., *Journal of Biological Chemistry*, 192:583-587, 1951; and Nakamura, *Agricultural and Biological Chemistry*, 32:701-706, 1968). Protein concentration was determined using Coomassie® Plus Protein Assay Reagent Kit (Pierce, USA) and SDS-PAGE. One unit of enzyme activity is defined as the amount of enzyme that produces xylulose from 1 µmole of D-xylose per min under the assay condition. Table 2 below shows the specific activity of wild-type glucose isomerase.

Example 19

Activity Assay of Glucose Isomerase Mutants

The activities of glucose isomerase mutant MGI4-35 and other mutants were measured as described in Example 18. Table 2 below shows the comparison of the specific activities of wild-type glucose isomerase and the mutants.

TABLE 2

The Specific Activities of Wild-type Glucose Isomerase and the Mutants

| Enzyme | SEQ ID NO. of the Amino Acid Sequence | Relative Specific Activity (%) |
| --- | --- | --- |
| Wild-type | SEQ ID NO.: 2 | 100.0 |
| MGI-W139F | SEQ ID NO.: 5 | 169.3 |
| MGI-F187S | SEQ ID NO.: 7 | 217.6 |
| MGI-T299Q | SEQ ID NO.: 8 | 192.4 |
| MGI-2 | SEQ ID NO.: 9 | 166.8 |
| MGI-3 | SEQ ID NO.: 10 | 190.9 |
| MGI-4 | SEQ ID NO.: 11 | 273.4 |
| MGI4-F139S | SEQ ID NO.: 12 | 329.6 |
| MGI4-F139K | SEQ ID NO.: 13 | 238.2 |
| MGI4-F139C | SEQ ID NO.: 14 | 219.7 |
| MGI4-F139I | SEQ ID NO.: 15 | 334.9 |
| MGI4-F139T | SEQ ID NO.: 16 | 314.0 |
| MGI4-F139N | SEQ ID NO.: 17 | 322.7 |
| MGI4-F139D | SEQ ID NO.: 18 | 212.4 |
| MGI4-A182P | SEQ ID NO.: 19 | 227.4 |
| MGI4-A182S | SEQ ID NO.: 20 | 333.1 |
| MGI4-A182I | SEQ ID NO.: 21 | 253.6 |
| MGI4-A182T | SEQ ID NO.: 22 | 288.8 |
| MGI4-A182V | SEQ ID NO.: 23 | 307.4 |
| MGI4-S187G | SEQ ID NO.: 24 | 393.9 |
| MGI4-S187A | SEQ ID NO.: 25 | 327.2 |
| MGI4-S187P | SEQ ID NO.: 26 | 186.9 |
| MGI4-Q299I | SEQ ID NO.: 27 | 153.5 |
| MGI4-Q299Y | SEQ ID NO.: 28 | 255.5 |
| MGI4-Q299C | SEQ ID NO.: 29 | 265.5 |
| MGI4-Q299M | SEQ ID NO.: 30 | 246.6 |
| MGI4-Q299E | SEQ ID NO.: 31 | 292.9 |
| MGI4-F87L | SEQ ID NO.: 32 | 170.7 |
| MGI4-F87M | SEQ ID NO.: 33 | 457.2 |
| MGI4-V217R | SEQ ID NO.: 34 | 209.4 |
| MGI4-D260E | SEQ ID NO.: 35 | 344.2 |
| MGI4-F276G | SEQ ID NO.: 36 | 378.3 |
| MGI4-24 | SEQ ID NO.: 37 | 154.0 |
| MGI4-25 | SEQ ID NO.: 38 | 255.4 |
| MGI4-34 | SEQ ID NO.: 39 | 405.9 |
| MGI4-35 | SEQ ID NO.: 40 | 396.3 |

Example 20

Thermostability of Wild-Type Glucose Isomerase

Two hundred μl of the partially purified wild-type glucose isomerase obtained as described in Example 16 were added to each of seven 1.5 ml microfuge tubes, and overlaid with 200 μl mineral oil. The tubes were placed in an 80° C. water bath. One of the seven tubes was removed from the water bath at a time interval of 0 h, 4 h, 12 h and 24 h, and centrifuged at 17,800 g for 20 min at 10° C. The residual protein and the residual glucose isomerase activity of the supernatants were determined as described in Example 18. FIG. 1 shows the thermostability of wild-type glucose isomerase at 80° C.

Example 21

Thermostability of Glucose Isomerase Mutants

The thermostability of glucose isomerase mutants MGI-4, MGI4-34 or MGI4-35 was measured as described in Example 20 and was shown in FIG. 1. As shown in FIG. 1, the half-life of the activity of wild-type glucose isomerase at 80° C. was 13.4 hours, that of MGI-4 was 21.4 hours, that of MGI4-34 was 19.2 hours and that of MGI4-35 was greater than 24 hours.

This invention is not limited by the detailed description in the Examples above. Various modifications can be made by those skilled in the art without departing from the scope of the invention.

The invention claimed is:

1. A method of making bioethanol comprising the step of using a glucose isomerase mutant to convert D-xylose to xylulose during the degradation of cellulose or hemicellulose to bioethanol, wherein an amino acid sequence of the glucose isomerase mutant is selected from the group consisting of SEQ ID NOs: 12-40; and wherein the glucose isomerase mutant has a catalytic activity at least 50% higher than that of a wild-type glucose isomerase in the conversion to xylulose using D-xylose as substrate.

* * * * *

SEQUENCE LISTING

<160> NUMBER OF SEQ ID NOS: 40

<210> SEQ ID NO 1
<211> LENGTH: 1320
<212> TYPE: DNA
<213> ORGANISM: Thermoanaerobacterium saccharolyticum

<400> SEQUENCE: 1

```
atgaataaat attttgagaa cgtatctaaa ataaaatatg aaggaccaaa atcaaataat      60
ccttattcct ttaaatttta caatccagag gaagtaatcg atggcaagac gatggaggag     120
catctccgct tttctatagc ttattggcac acttttactg ctgatggaac agatcaattt     180
ggcaaggcta ctatgcaaag accatggaac cactacacag atcctatgga tatagcgaaa     240
gcaagggtag aagcagcatt tgagtttttt gataagataa atgcaccttt cttctgcttc     300
catgataggg atattgcccc tgaaggagat actcttagag agacaaacaa aaacttagat     360
acaatagttg ctatgataaa ggattactta aagaccagca agacaaaagt tttgtggggt     420
accgcaaatc ttttctccaa tccgagattt gtacatggtg catcaacatc ctgcaatgct     480 gacgttttg catattctgc agcgcaagtc aaaaaagccc ttgagattac taaggagctt     540
ggccgcgaaa actacgtatt tgggggtgga agagaaggggt acgagacgct tctcaataca     600
gatatggagt tagagcttga taactttgca agattttgc acatggctgt tgactatgca     660
```

-continued

```
aaggaaatcg gctttgaagg tcagttcttg attgagccga agccaaagga gcctacaaaa    720
catcaatacg actttgacgt ggcaaatgta ttggcattct tgagaaaata cgaccttgac    780
aaatatttca agtaaatat cgaagcaaac catgcgacat tggcattcca cgacttccaa     840
catgagctaa gatacgccag aataaacggt gtattaggat caattgacgc aaatacaggc    900
gacatgcttt tgggatggga tacggaccag ttccctacag atatacgcat gacaacgctt    960
gctatgtatg aagtcataaa gatgggtgga tttgacaaag gtggccttaa ctttgatgca   1020
aaagtaagac gtgcttcatt tgagccagaa gatcttttct taggtcacat agcaggaatg   1080
gatgcttttg caaaaggctt taagttgct tacaagcttg tgaaagatgg cgtatttgac    1140
aagttcatcg aagaaagata cgcaagctac aaagaaggca ttggcgctga tattgtaagc   1200
ggtaaagctg acttcaagag ccttgaaaag tatgcattag agcacagcca gattgtaaac   1260
aaatcaggca gacaagagct attagaatca atcctaaatc agtatttgtt tgcagaataa   1320
```

<210> SEQ ID NO 2
<211> LENGTH: 439
<212> TYPE: PRT
<213> ORGANISM: Thermoanaerobacterium saccharolyticum

<400> SEQUENCE: 2

```
Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
                20                  25                  30

Ile Asp Gly Lys Thr Met Glu Glu His Leu Arg Phe Ser Ile Ala Tyr
            35                  40                  45

Trp His Thr Phe Thr Ala Asp Gly Thr Asp Gln Phe Gly Lys Ala Thr
        50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Trp Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Arg Glu Asn Tyr Val Phe Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Val Asp Tyr Ala Lys Glu Ile Gly
    210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
```

```
                        260                 265                 270
Thr Leu Ala Phe His Asp Phe Gln His Glu Leu Arg Tyr Ala Arg Ile
        275                 280                 285

Asn Gly Val Leu Gly Ser Ile Asp Ala Asn Thr Gly Asp Met Leu Leu
        290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
    370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
            420                 425                 430

Asn Gln Tyr Leu Phe Ala Glu
        435

<210> SEQ ID NO 3
<211> LENGTH: 1320
<212> TYPE: DNA
<213> ORGANISM: Thermoanaerobacterium saccharolyticum
<220> FEATURE:
<221> NAME/KEY: misc_feature
<222> LOCATION: (259)..(261)
<223> OTHER INFORMATION: "n" represents a,t,g or c; and "nnn" represents
      any amino acid code except for phenylalanine.
<220> FEATURE:
<221> NAME/KEY: misc_feature
<222> LOCATION: (415)..(417)
<223> OTHER INFORMATION: "n" represents a,t,g or c; and "nnn" represents
      any amino acid code except for typtophan.
<220> FEATURE:
<221> NAME/KEY: misc_feature
<222> LOCATION: (544)..(546)
<223> OTHER INFORMATION: "n" represents a,t,g or c; and "nnn" represents
      any amino acid code except for Arginine.
<220> FEATURE:
<221> NAME/KEY: misc_feature
<222> LOCATION: (559)..(561)
<223> OTHER INFORMATION: "n" represents a,t,g or c; and "nnn" represents
      any amino acid code except for phenylalanine.
<220> FEATURE:
<221> NAME/KEY: misc_feature
<222> LOCATION: (649)..(651)
<223> OTHER INFORMATION: "n" represents a,t,g or c; and "nnn" represents
      any amino acid code except for valine.
<220> FEATURE:
<221> NAME/KEY: misc_feature
<222> LOCATION: (778)..(780)
<223> OTHER INFORMATION: "n" represents a,t,g or c; and "nnn" represents
      any amino acid code except for aspartic acid.
<220> FEATURE:
<221> NAME/KEY: misc_feature
<222> LOCATION: (826)..(828)
<223> OTHER INFORMATION: "n" represents a,t,g or c; and "nnn" represents
      any amino acid code except for phenylalanine.
<220> FEATURE:
<221> NAME/KEY: misc_feature
<222> LOCATION: (895)..(897)
<223> OTHER INFORMATION: "n" represents a,t,g or c; and "nnn" represents
      any amino acid code except for threonine.
```

-continued

```
<400> SEQUENCE: 3
atgaataaat attttgagaa cgtatctaaa ataaaatatg aaggaccaaa atcaaataat      60
ccttattcct ttaaatttta caatccagag gaagtaatcg atggcaagac gatggaggag    120
catctccgct tttctatagc ttattggcac acttttactg ctgatggaac agatcaattt    180
ggcaaggcta ctatgcaaag accatggaac cactacacag atcctatgga tatagcgaaa    240
gcaagggtag aagcagcann ngagtttttt gataagataa atgcaccttt cttctgcttc    300
catgataggg atattgcccc tgaaggagat actcttagag agacaaacaa aaacttagat    360
acaatagttg ctatgataaa ggattactta aagaccagca agacaaaagt tttgnnnggt    420
accgcaaatc ttttctccaa tccgagattt gtacatggtg catcaacatc ctgcaatgct    480 gacgttttg catattctgc agcgcaagtc aaaaaagccc ttgagattac taaggagctt     540
ggcnnngaaa actacgtann ntggggtgga agagaagggt acgagacgct tctcaataca    600
gatatggagt tagagcttga taactttgca agattttgc acatggctnn ngactatgca    660
aaggaaatcg gctttgaagg tcagttcttg attgagccga agccaaagga gcctacaaaa    720
catcaatacg acttttgacgt ggcaaatgta ttggcattct tgagaaaata cgaccttnnn    780
aaatatttca agtaaatat cgaagcaaac catgcgacat tggcannnca cgacttccaa    840
catgagctaa gatacgccag aataaacggt gtattaggat caattgacgc aaatnnnggc    900
gacatgcttt tgggatggga tacggaccag ttccctacag atatacgcat gacaacgctt    960
gctatgtatg aagtcataaa gatgggtgga tttgacaaag gtggccttaa ctttgatgca   1020
aaagtaagac gtgcttcatt tgagccagaa gatctttcct taggtcacat agcaggaatg   1080
gatgcttttg caaaaggctt taagttgct tacaagcttg tgaaagatgg cgtatttgac    1140
aagttcatcg aagaaagata cgcaagctac aaagaaggca ttggcgctga tattgtaagc   1200
ggtaaagctg acttcaagag ccttgaaaag tatgcattag agcacagcca gattgtaaac   1260
aaatcaggca gacaagagct attagaatca atcctaaatc agtatttgtt tgcagaataa   1320
```

```
<210> SEQ ID NO 4
<211> LENGTH: 439
<212> TYPE: PRT
<213> ORGANISM: Thermoanaerobacterium saccharolyticum
<220> FEATURE:
<221> NAME/KEY: MISC_FEATURE
<222> LOCATION: (87)..(87)
<223> OTHER INFORMATION: Xaa represents any amino acid residue other
      than phenylalanine.
<220> FEATURE:
<221> NAME/KEY: MISC_FEATURE
<222> LOCATION: (139)..(139)
<223> OTHER INFORMATION: Xaa represents any amino acid residue other
      than tryptophan.
<220> FEATURE:
<221> NAME/KEY: MISC_FEATURE
<222> LOCATION: (182)..(182)
<223> OTHER INFORMATION: Xaa represents any amino acid residue other
      than Arginine.
<220> FEATURE:
<221> NAME/KEY: MISC_FEATURE
<222> LOCATION: (187)..(187)
<223> OTHER INFORMATION: Xaa represents any amino acid residue other
      than phenylalanine.
<220> FEATURE:
<221> NAME/KEY: MISC_FEATURE
<222> LOCATION: (217)..(217)
<223> OTHER INFORMATION: Xaa represents any amino acid residue other
      than valine.
<220> FEATURE:
<221> NAME/KEY: MISC_FEATURE
<222> LOCATION: (260)..(260)
```

```
<223> OTHER INFORMATION: Xaa represents any amino acid residue other
      than aspartic acid.
<220> FEATURE:
<221> NAME/KEY: MISC_FEATURE
<222> LOCATION: (276)..(276)
<223> OTHER INFORMATION: Xaa represents any amino acid residue other
      than phenylalanine.
<220> FEATURE:
<221> NAME/KEY: MISC_FEATURE
<222> LOCATION: (299)..(299)
<223> OTHER INFORMATION: Xaa represents any amino acid residue other
      than threonine.

<400> SEQUENCE: 4

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
        35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Xaa Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Xaa Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Xaa Glu Asn Tyr Val Xaa Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Xaa Asp Tyr Ala Lys Glu Ile Gly
    210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Xaa Lys Tyr Phe Lys Val Asn Ile Glu Ala Asn His Ala
            260                 265                 270

Thr Leu Ala Xaa His Asp Phe Gln His Glu Leu Arg Tyr Ala Arg Ile
        275                 280                 285

Asn Gly Val Leu Gly Ser Ile Asp Ala Asn Xaa Gly Asp Met Leu Leu
    290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350
```

```
Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
        370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
            420                 425                 430

Asn Gln Tyr Leu Phe Ala Glu
            435

<210> SEQ ID NO 5
<211> LENGTH: 439
<212> TYPE: PRT
<213> ORGANISM: Thermoanaerobacterium saccharolyticum

<400> SEQUENCE: 5

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
        35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Phe Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Arg Glu Asn Tyr Val Phe Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Val Asp Tyr Ala Lys Glu Ile Gly
    210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285
```

```
Asn Gly Val Leu Gly Ser Ile Asp Ala Asn Thr Gly Asp Met Leu Leu
    290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
    370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
            420                 425                 430

Asn Gln Tyr Leu Phe Ala Glu
        435

<210> SEQ ID NO 6
<211> LENGTH: 439
<212> TYPE: PRT
<213> ORGANISM: Thermoanaerobacterium saccharolyticum

<400> SEQUENCE: 6

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
        35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Trp Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Ala Glu Asn Tyr Val Phe Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Val Asp Tyr Ala Lys Glu Ile Gly
    210                 215                 220
```

```
Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
            245                 250                 255

Tyr Asp Leu Asp Lys Tyr Phe Lys Val Asn Ile Glu Ala Asn His Ala
        260                 265                 270

Thr Leu Ala Phe His Asp Phe Gln His Glu Leu Arg Tyr Ala Arg Ile
    275                 280                 285

Asn Gly Val Leu Gly Ser Ile Asp Ala Asn Thr Gly Asp Met Leu Leu
290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
            325                 330                 335

Asn Phe Asp Ala Lys Val Arg Arg Ala Ser Phe Glu Pro Glu Asp Leu
        340                 345                 350

Phe Leu Gly His Ile Ala Gly Met Asp Ala Phe Ala Lys Gly Phe Lys
    355                 360                 365

Val Ala Tyr Lys Leu Val Lys Asp Gly Val Phe Asp Lys Phe Ile Glu
370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
            405                 410                 415

Gln Ile Val Asn Lys Ser Gly Arg Gln Glu Leu Leu Glu Ser Ile Leu
        420                 425                 430

Asn Gln Tyr Leu Phe Ala Glu
        435

<210> SEQ ID NO 7
<211> LENGTH: 439
<212> TYPE: PRT
<213> ORGANISM: Thermoanaerobacterium saccharolyticum

<400> SEQUENCE: 7

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
        35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Trp Gly Thr Ala Asn Leu
    130                 135                 140

Phe Ser Asn Pro Arg Phe Val His Gly Ala Ser Thr Ser Cys Asn Ala
145                 150                 155                 160
```

```
Asp Val Phe Ala Tyr Ser Ala Ala Gln Val Lys Lys Ala Leu Glu Ile
                165                 170                 175

Thr Lys Glu Leu Gly Arg Glu Asn Tyr Val Ser Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Val Asp Tyr Ala Lys Glu Ile Gly
    210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285

Asn Gly Val Leu Gly Ser Ile Asp Ala Asn Thr Gly Asp Met Leu Leu
    290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
    370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
            420                 425                 430

Asn Gln Tyr Leu Phe Ala Glu
        435

<210> SEQ ID NO 8
<211> LENGTH: 439
<212> TYPE: PRT
<213> ORGANISM: Thermoanaerobacterium saccharolyticum

<400> SEQUENCE: 8

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
        35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
                85                  90                  95
```

```
Phe Phe Cys Phe His Asp Arg Asp Ile Ala Pro Glu Gly Asp Thr Leu
                100                 105                 110

Arg Glu Thr Asn Lys Asn Leu Asp Thr Ile Val Ala Met Ile Lys Asp
            115                 120                 125

Tyr Leu Lys Thr Ser Lys Thr Lys Val Leu Trp Gly Thr Ala Asn Leu
130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Arg Glu Asn Tyr Val Phe Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Val Asp Tyr Ala Lys Glu Ile Gly
210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285

Asn Gly Val Leu Gly Ser Ile Asp Ala Asn Gln Gly Asp Met Leu Leu
290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
            420                 425                 430

Asn Gln Tyr Leu Phe Ala Glu
        435

<210> SEQ ID NO 9
<211> LENGTH: 439
<212> TYPE: PRT
<213> ORGANISM: Thermoanaerobacter lactoethylicum

<400> SEQUENCE: 9

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30
```

-continued

Ile Asp Gly Lys Thr Met Glu Glu His Leu Arg Phe Ser Ile Ala Tyr
         35                  40                  45

Trp His Thr Phe Thr Ala Asp Gly Thr Asp Gln Phe Gly Lys Ala Thr
 50                  55                  60

Met Gln Arg Pro Trp Asn His Tyr Thr Asp Pro Met Asp Ile Ala Lys
 65                  70                  75                  80

Ala Arg Val Glu Ala Ala Phe Glu Phe Phe Asp Lys Ile Asn Ala Pro
                 85                  90                  95

Phe Phe Cys Phe His Asp Arg Asp Ile Ala Pro Glu Gly Asp Thr Leu
                100                 105                 110

Arg Glu Thr Asn Lys Asn Leu Asp Thr Ile Val Ala Met Ile Lys Asp
                115                 120                 125

Tyr Leu Lys Thr Ser Lys Thr Lys Val Leu Phe Gly Thr Ala Asn Leu
        130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Ala Glu Asn Tyr Val Phe Trp Gly Gly Arg Glu
                180                 185                 190

Gly Tyr Glu Thr Leu Leu Asn Thr Asp Met Glu Leu Glu Leu Asp Asn
        195                 200                 205

Phe Ala Arg Phe Leu His Met Ala Val Asp Tyr Ala Lys Glu Ile Gly
        210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
                260                 265                 270

Thr Leu Ala Phe His Asp Phe Gln His Glu Leu Arg Tyr Ala Arg Ile
        275                 280                 285

Asn Gly Val Leu Gly Ser Ile Asp Ala Asn Thr Gly Asp Met Leu Leu
        290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
                340                 345                 350

Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
        370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
                420                 425                 430

Asn Gln Tyr Leu Phe Ala Glu
        435

<210> SEQ ID NO 10
<211> LENGTH: 439
<212> TYPE: PRT
<213> ORGANISM: Thermoanaerobacter lactoethylicum

<400> SEQUENCE: 10

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
        35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Phe Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Ala Glu Asn Tyr Val Phe Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Val Asp Tyr Ala Lys Glu Ile Gly
    210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285

Asn Gly Val Leu Gly Ser Ile Asp Ala Asn Gln Gly Asp Met Leu Leu
    290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
    370                 375                 380

Glu Arg Tyr Ala Ser Tyr Lys Glu Gly Ile Gly Ala Asp Ile Val Ser

```
                385                 390                 395                 400
Gly Lys Ala Asp Phe Lys Ser Leu Glu Lys Tyr Ala Leu Glu His Ser
                    405                 410                 415

Gln Ile Val Asn Lys Ser Gly Arg Gln Glu Leu Leu Glu Ser Ile Leu
                420                 425                 430

Asn Gln Tyr Leu Phe Ala Glu
            435

<210> SEQ ID NO 11
<211> LENGTH: 439
<212> TYPE: PRT
<213> ORGANISM: Thermoanaerobacterium saccharolyticum

<400> SEQUENCE: 11

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
                20                  25                  30

Ile Asp Gly Lys Thr Met Glu Glu His Leu Arg Phe Ser Ile Ala Tyr
            35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
                85                  90                  95

Phe Phe Cys Phe His Asp Arg Asp Ile Ala Pro Glu Gly Asp Thr Leu
                100                 105                 110

Arg Glu Thr Asn Lys Asn Leu Asp Thr Ile Val Ala Met Ile Lys Asp
            115                 120                 125

Tyr Leu Lys Thr Ser Lys Thr Lys Val Leu Phe Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Ala Glu Asn Tyr Val Ser Trp Gly Gly Arg Glu
            180                 185                 190

Gly Tyr Glu Thr Leu Leu Asn Thr Asp Met Glu Leu Glu Leu Asp Asn
    195                 200                 205

Phe Ala Arg Phe Leu His Met Ala Val Asp Tyr Ala Lys Glu Ile Gly
210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
    275                 280                 285

Asn Gly Val Leu Gly Ser Ile Asp Ala Asn Gln Gly Asp Met Leu Leu
290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
```

-continued

```
                325                 330                 335
Asn Phe Asp Ala Lys Val Arg Arg Ala Ser Phe Glu Pro Glu Asp Leu
            340                 345                 350
Phe Leu Gly His Ile Ala Gly Met Asp Ala Phe Ala Lys Gly Phe Lys
            355                 360                 365
Val Ala Tyr Lys Leu Val Lys Asp Gly Val Phe Asp Lys Phe Ile Glu
            370                 375                 380
Glu Arg Tyr Ala Ser Tyr Lys Glu Gly Ile Gly Ala Asp Ile Val Ser
385                 390                 395                 400
Gly Lys Ala Asp Phe Lys Ser Leu Glu Lys Tyr Ala Leu Glu His Ser
                405                 410                 415
Gln Ile Val Asn Lys Ser Gly Arg Gln Glu Leu Leu Glu Ser Ile Leu
            420                 425                 430
Asn Gln Tyr Leu Phe Ala Glu
            435

<210> SEQ ID NO 12
<211> LENGTH: 439
<212> TYPE: PRT
<213> ORGANISM: Thermoanaerobacterium saccharolyticum

<400> SEQUENCE: 12

Met Asn Lys Tyr Phe Glu Asn Val Ser Lys Ile Lys Tyr Glu Gly Pro
1               5                   10                  15
Lys Ser Asn Asn Pro Tyr Ser Phe Lys Phe Tyr Asn Pro Glu Glu Val
            20                  25                  30
Ile Asp Gly Lys Thr Met Glu Glu His Leu Arg Phe Ser Ile Ala Tyr
        35                  40                  45
Trp His Thr Phe Thr Ala Asp Gly Thr Asp Gln Phe Gly Lys Ala Thr
    50                  55                  60
Met Gln Arg Pro Trp Asn His Tyr Thr Asp Pro Met Asp Ile Ala Lys
65                  70                  75                  80
Ala Arg Val Glu Ala Ala Phe Glu Phe Phe Asp Lys Ile Asn Ala Pro
                85                  90                  95
Phe Phe Cys Phe His Asp Arg Asp Ile Ala Pro Glu Gly Asp Thr Leu
            100                 105                 110
Arg Glu Thr Asn Lys Asn Leu Asp Thr Ile Val Ala Met Ile Lys Asp
            115                 120                 125
Tyr Leu Lys Thr Ser Lys Thr Lys Val Leu Ser Gly Thr Ala Asn Leu
        130                 135                 140
Phe Ser Asn Pro Arg Phe Val His Gly Ala Ser Thr Ser Cys Asn Ala
145                 150                 155                 160
Asp Val Phe Ala Tyr Ser Ala Ala Gln Val Lys Lys Ala Leu Glu Ile
                165                 170                 175
Thr Lys Glu Leu Gly Ala Glu Asn Tyr Val Ser Trp Gly Gly Arg Glu
            180                 185                 190
Gly Tyr Glu Thr Leu Leu Asn Thr Asp Met Glu Leu Glu Leu Asp Asn
        195                 200                 205
Phe Ala Arg Phe Leu His Met Ala Val Asp Tyr Ala Lys Glu Ile Gly
    210                 215                 220
Phe Glu Gly Gln Phe Leu Ile Glu Pro Lys Pro Lys Glu Pro Thr Lys
225                 230                 235                 240
His Gln Tyr Asp Phe Asp Val Ala Asn Val Leu Ala Phe Leu Arg Lys
                245                 250                 255
Tyr Asp Leu Asp Lys Tyr Phe Lys Val Asn Ile Glu Ala Asn His Ala
```

```
                    260                 265                 270
Thr Leu Ala Phe His Asp Phe Gln His Glu Leu Arg Tyr Ala Arg Ile
            275                 280                 285

Asn Gly Val Leu Gly Ser Ile Asp Ala Asn Gln Gly Asp Met Leu Leu
            290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
            325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
            355                 360                 365

Val Ala Tyr Lys Leu Val Lys Asp Gly Val Phe Asp Lys Phe Ile Glu
            370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
            405                 410                 415

Gln Ile Val Asn Lys Ser Gly Arg Gln Glu Leu Leu Glu Ser Ile Leu
            420                 425                 430

Asn Gln Tyr Leu Phe Ala Glu
            435

<210> SEQ ID NO 13
<211> LENGTH: 439
<212> TYPE: PRT
<213> ORGANISM: Thermoanaerobacterium saccharolyticum

<400> SEQUENCE: 13

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
        35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Lys Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Ala Glu Asn Tyr Val Ser Trp Gly Gly Arg Glu
            180                 185                 190

Gly Tyr Glu Thr Leu Leu Asn Thr Asp Met Glu Leu Glu Leu Asp Asn
```

```
                195                 200                 205
Phe Ala Arg Phe Leu His Met Ala Val Asp Tyr Ala Lys Glu Ile Gly
            210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285

Asn Gly Val Leu Gly Ser Ile Asp Ala Asn Gln Gly Asp Met Leu Leu
    290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
    370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
            420                 425                 430

Asn Gln Tyr Leu Phe Ala Glu
        435

<210> SEQ ID NO 14
<211> LENGTH: 439
<212> TYPE: PRT
<213> ORGANISM: Thermoanaerobacterium saccharolyticum

<400> SEQUENCE: 14

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu His Leu Arg Phe Ser Ile Ala Tyr
        35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Cys Gly Thr Ala Asn Leu
```

```
                130              135              140
Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Ala Glu Asn Tyr Val Ser Trp Gly Gly Arg Glu
            180                 185                 190

Gly Tyr Glu Thr Leu Leu Asn Thr Asp Met Glu Leu Leu Asp Asn
            195                 200                 205

Phe Ala Arg Phe Leu His Met Ala Val Asp Tyr Ala Lys Glu Ile Gly
            210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
                260                 265                 270

Thr Leu Ala Phe His Asp Phe Gln His Glu Leu Arg Tyr Ala Arg Ile
            275                 280                 285

Asn Gly Val Leu Gly Ser Ile Asp Ala Asn Gln Gly Asp Met Leu Leu
            290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
            355                 360                 365

Val Ala Tyr Lys Leu Val Lys Asp Gly Val Phe Asp Lys Phe Ile Glu
            370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Gly Ser Ile Leu
                420                 425                 430

Asn Gln Tyr Leu Phe Ala Glu
            435

<210> SEQ ID NO 15
<211> LENGTH: 439
<212> TYPE: PRT
<213> ORGANISM: Thermoanaerobacterium saccharolyticum

<400> SEQUENCE: 15

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
                20                  25                  30

Ile Asp Gly Lys Thr Met Glu Glu His Leu Arg Phe Ser Ile Ala Tyr
            35                  40                  45

Trp His Thr Phe Thr Ala Asp Gly Thr Asp Gln Phe Gly Lys Ala Thr
        50                  55                  60

Met Gln Arg Pro Trp Asn His Tyr Thr Asp Pro Met Asp Ile Ala Lys
```

```
                65                  70                  75                  80
Ala Arg Val Glu Ala Ala Phe Glu Phe Asp Lys Ile Asn Ala Pro
                    85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Ile Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Ala Glu Asn Tyr Val Ser Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Val Asp Tyr Ala Lys Glu Ile Gly
    210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285

Asn Gly Val Leu Gly Ser Ile Asp Ala Asn Gln Gly Asp Met Leu Leu
    290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
    370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
            420                 425                 430

Asn Gln Tyr Leu Phe Ala Glu
        435

<210> SEQ ID NO 16
<211> LENGTH: 439
<212> TYPE: PRT
<213> ORGANISM: Thermoanaerobacterium saccharolyticum

<400> SEQUENCE: 16

Met Asn Lys Tyr Phe Glu Asn Val Ser Lys Ile Lys Tyr Glu Gly Pro
```

-continued

```
1               5                   10                  15
Lys Ser Asn Asn Pro Tyr Ser Phe Lys Phe Tyr Asn Pro Glu Glu Val
                20                  25                  30

Ile Asp Gly Lys Thr Met Glu Glu His Leu Arg Phe Ser Ile Ala Tyr
            35                  40                  45

Trp His Thr Phe Thr Ala Asp Gly Thr Asp Gln Phe Gly Lys Ala Thr
        50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Thr Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Ala Glu Asn Tyr Val Ser Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Val Asp Tyr Ala Lys Glu Ile Gly
    210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285

Asn Gly Val Leu Gly Ser Ile Asp Ala Asn Gln Gly Asp Met Leu Leu
    290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
    370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
            420                 425                 430
```

Asn Gln Tyr Leu Phe Ala Glu
        435

<210> SEQ ID NO 17
<211> LENGTH: 439
<212> TYPE: PRT
<213> ORGANISM: Thermoanaerobacterium saccharolyticum

<400> SEQUENCE: 17

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
        35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Asn Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Ala Glu Asn Tyr Val Ser Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Val Asp Tyr Ala Lys Glu Ile Gly
    210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285

Asn Gly Val Leu Gly Ser Ile Asp Ala Asn Gln Gly Asp Met Leu Leu
    290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
        355                 360                 365

```
Val Ala Tyr Lys Leu Val Lys Asp Gly Val Phe Asp Lys Phe Ile Glu
        370                 375                 380
Glu Arg Tyr Ala Ser Tyr Lys Glu Gly Ile Gly Ala Asp Ile Val Ser
385                 390                 395                 400
Gly Lys Ala Asp Phe Lys Ser Leu Glu Lys Tyr Ala Leu Glu His Ser
                405                 410                 415
Gln Ile Val Asn Lys Ser Gly Arg Gln Glu Leu Leu Glu Ser Ile Leu
            420                 425                 430
Asn Gln Tyr Leu Phe Ala Glu
            435

<210> SEQ ID NO 18
<211> LENGTH: 439
<212> TYPE: PRT
<213> ORGANISM: Thermoanaerobacterium saccharolyticum

<400> SEQUENCE: 18

Met Asn Lys Tyr Phe Glu Asn Val Ser Lys Ile Lys Tyr Glu Gly Pro
1               5                   10                  15
Lys Ser Asn Asn Pro Tyr Ser Phe Lys Phe Tyr Asn Pro Glu Glu Val
                20                  25                  30
Ile Asp Gly Lys Thr Met Glu Glu His Leu Arg Phe Ser Ile Ala Tyr
            35                  40                  45
Trp His Thr Phe Thr Ala Asp Gly Thr Asp Gln Phe Gly Lys Ala Thr
    50                  55                  60
Met Gln Arg Pro Trp Asn His Tyr Thr Asp Pro Met Asp Ile Ala Lys
65                  70                  75                  80
Ala Arg Val Glu Ala Ala Phe Glu Phe Phe Asp Lys Ile Asn Ala Pro
                85                  90                  95
Phe Phe Cys Phe His Asp Arg Asp Ile Ala Pro Glu Gly Asp Thr Leu
            100                 105                 110
Arg Glu Thr Asn Lys Asn Leu Asp Thr Ile Val Ala Met Ile Lys Asp
        115                 120                 125
Tyr Leu Lys Thr Ser Lys Thr Lys Val Leu Asp Gly Thr Ala Asn Leu
    130                 135                 140
Phe Ser Asn Pro Arg Phe Val His Gly Ala Ser Thr Ser Cys Asn Ala
145                 150                 155                 160
Asp Val Phe Ala Tyr Ser Ala Ala Gln Val Lys Lys Ala Leu Glu Ile
                165                 170                 175
Thr Lys Glu Leu Gly Ala Glu Asn Tyr Val Ser Trp Gly Gly Arg Glu
            180                 185                 190
Gly Tyr Glu Thr Leu Leu Asn Thr Asp Met Glu Leu Glu Leu Asp Asn
        195                 200                 205
Phe Ala Arg Phe Leu His Met Ala Val Asp Tyr Ala Lys Glu Ile Gly
    210                 215                 220
Phe Glu Gly Gln Phe Leu Ile Glu Pro Lys Pro Lys Glu Pro Thr Lys
225                 230                 235                 240
His Gln Tyr Asp Phe Asp Val Ala Asn Val Leu Ala Phe Leu Arg Lys
                245                 250                 255
Tyr Asp Leu Asp Lys Tyr Phe Lys Val Asn Ile Glu Ala Asn His Ala
            260                 265                 270
Thr Leu Ala Phe His Asp Phe Gln His Glu Leu Arg Tyr Ala Arg Ile
        275                 280                 285
Asn Gly Val Leu Gly Ser Ile Asp Ala Asn Gln Gly Asp Met Leu Leu
    290                 295                 300
```

```
Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
            325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
            355                 360                 365

Val Ala Tyr Lys Leu Val Lys Asp Gly Val Phe Asp Lys Phe Ile Glu
            370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
            405                 410                 415

Gln Ile Val Asn Lys Ser Gly Arg Gln Glu Leu Leu Glu Ser Ile Leu
            420                 425                 430

Asn Gln Tyr Leu Phe Ala Glu
            435
```

```
<210> SEQ ID NO 19
<211> LENGTH: 439
<212> TYPE: PRT
<213> ORGANISM: Thermoanaerobacterium saccharolyticum

<400> SEQUENCE: 19

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
            35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
            115                 120                 125

Tyr Leu Lys Thr Ser Lys Thr Lys Val Leu Phe Gly Thr Ala Asn Leu
            130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Pro Glu Asn Tyr Val Ser Trp Gly Gly Arg Glu
            180                 185                 190

Gly Tyr Glu Thr Leu Leu Asn Thr Asp Met Glu Leu Glu Leu Asp Asn
            195                 200                 205

Phe Ala Arg Phe Leu His Met Ala Val Asp Tyr Ala Lys Glu Ile Gly
            210                 215                 220

Phe Glu Gly Gln Phe Leu Ile Glu Pro Lys Pro Lys Glu Pro Thr Lys
225                 230                 235                 240
```

```
His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285

Asn Gly Val Leu Gly Ser Ile Asp Ala Asn Gln Gly Asp Met Leu Leu
    290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
    370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
            420                 425                 430

Asn Gln Tyr Leu Phe Ala Glu
            435

<210> SEQ ID NO 20
<211> LENGTH: 439
<212> TYPE: PRT
<213> ORGANISM: Thermoanaerobacterium saccharolyticum

<400> SEQUENCE: 20

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
                20                  25                  30

Ile Asp Gly Lys Thr Met Glu Glu His Leu Arg Phe Ser Ile Ala Tyr
            35                  40                  45

Trp His Thr Phe Thr Ala Asp Gly Thr Asp Gln Phe Gly Lys Ala Thr
        50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Phe Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175
```

```
Thr Lys Glu Leu Gly Ser Glu Asn Tyr Val Ser Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Val Asp Tyr Ala Lys Glu Ile Gly
    210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285

Asn Gly Val Leu Gly Ser Ile Asp Ala Asn Gln Gly Asp Met Leu Leu
    290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
    370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
            420                 425                 430

Asn Gln Tyr Leu Phe Ala Glu
        435

<210> SEQ ID NO 21
<211> LENGTH: 439
<212> TYPE: PRT
<213> ORGANISM: Thermoanaerobacterium saccharolyticum

<400> SEQUENCE: 21

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
        35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110
```

Arg Glu Thr Asn Lys Asn Leu Asp Thr Ile Val Ala Met Ile Lys Asp
            115                 120                 125

Tyr Leu Lys Thr Ser Lys Thr Lys Val Leu Phe Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Ile Glu Asn Tyr Val Ser Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Val Asp Tyr Ala Lys Glu Ile Gly
    210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285

Asn Gly Val Leu Gly Ser Ile Asp Ala Asn Gln Gly Asp Met Leu Leu
    290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
    370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
            420                 425                 430

Asn Gln Tyr Leu Phe Ala Glu
        435

<210> SEQ ID NO 22
<211> LENGTH: 439
<212> TYPE: PRT
<213> ORGANISM: Thermoanaerobacterium saccharolyticum

<400> SEQUENCE: 22

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
        35                  40                  45

Trp His Thr Phe Thr Ala Asp Gly Thr Asp Gln Phe Gly Lys Ala Thr
 50                  55                  60

Met Gln Arg Pro Trp Asn His Tyr Thr Asp Pro Met Asp Ile Ala Lys
 65                  70                  75                  80

Ala Arg Val Glu Ala Ala Phe Glu Phe Asp Lys Ile Asn Ala Pro
                 85                  90                  95

Phe Phe Cys Phe His Asp Arg Asp Ile Ala Pro Glu Gly Asp Thr Leu
                100                 105                 110

Arg Glu Thr Asn Lys Asn Leu Asp Thr Ile Val Ala Met Ile Lys Asp
             115                 120                 125

Tyr Leu Lys Thr Ser Lys Thr Lys Val Leu Phe Gly Thr Ala Asn Leu
             130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                 165                 170                 175

Thr Lys Glu Leu Gly Thr Glu Asn Tyr Val Ser Trp Gly Gly Arg Glu
             180                 185                 190

Gly Tyr Glu Thr Leu Leu Asn Thr Asp Met Glu Leu Glu Leu Asp Asn
             195                 200                 205

Phe Ala Arg Phe Leu His Met Ala Val Asp Tyr Ala Lys Glu Ile Gly
             210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                 245                 250                 255

Tyr Asp Leu Asp Lys Tyr Phe Lys Val Asn Ile Glu Ala Asn His Ala
             260                 265                 270

Thr Leu Ala Phe His Asp Phe Gln His Glu Leu Arg Tyr Ala Arg Ile
             275                 280                 285

Asn Gly Val Leu Gly Ser Ile Asp Ala Asn Gln Gly Asp Met Leu Leu
             290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                 325                 330                 335

Asn Phe Asp Ala Lys Val Arg Arg Ala Ser Phe Glu Pro Glu Asp Leu
             340                 345                 350

Phe Leu Gly His Ile Ala Gly Met Asp Ala Phe Ala Lys Gly Phe Lys
             355                 360                 365

Val Ala Tyr Lys Leu Val Lys Asp Gly Val Phe Asp Lys Phe Ile Glu
             370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                 405                 410                 415

Gln Ile Val Asn Lys Ser Gly Arg Gln Glu Leu Leu Glu Ser Ile Leu
             420                 425                 430

Asn Gln Tyr Leu Phe Ala Glu
             435

<210> SEQ ID NO 23
<211> LENGTH: 439
<212> TYPE: PRT
<213> ORGANISM: Thermoanaerobacterium saccharolyticum

<400> SEQUENCE: 23

```
Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
        35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Phe Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Val Glu Asn Tyr Val Ser Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Val Asp Tyr Ala Lys Glu Ile Gly
    210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285

Asn Gly Val Leu Gly Ser Ile Asp Ala Asn Gln Gly Asp Met Leu Leu
    290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
    370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415
```

Gln Ile Val Asn Lys Ser Gly Arg Gln Glu Leu Leu Glu Ser Ile Leu
            420                 425                 430

Asn Gln Tyr Leu Phe Ala Glu
        435

<210> SEQ ID NO 24
<211> LENGTH: 439
<212> TYPE: PRT
<213> ORGANISM: Thermoanaerobacterium saccharolyticum

<400> SEQUENCE: 24

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
        35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Phe Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Ala Glu Asn Tyr Val Gly Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Val Asp Tyr Ala Lys Glu Ile Gly
    210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285

Asn Gly Val Leu Gly Ser Ile Asp Ala Asn Gln Gly Asp Met Leu Leu
    290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

```
Phe Leu Gly His Ile Ala Gly Met Asp Ala Phe Ala Lys Gly Phe Lys
            355                 360                 365

Val Ala Tyr Lys Leu Val Lys Asp Gly Val Phe Asp Lys Phe Ile Glu
    370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
            420                 425                 430

Asn Gln Tyr Leu Phe Ala Glu
            435
```

<210> SEQ ID NO 25
<211> LENGTH: 439
<212> TYPE: PRT
<213> ORGANISM: Thermoanaerobacterium saccharolyticum

<400> SEQUENCE: 25

```
Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
        35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Phe Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Ala Glu Asn Tyr Val Ala Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Val Asp Tyr Ala Lys Glu Ile Gly
    210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285
```

Asn Gly Val Leu Gly Ser Ile Asp Ala Asn Gln Gly Asp Met Leu Leu
    290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
    370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
            420                 425                 430

Asn Gln Tyr Leu Phe Ala Glu
        435

<210> SEQ ID NO 26
<211> LENGTH: 439
<212> TYPE: PRT
<213> ORGANISM: Thermoanaerobacterium saccharolyticum

<400> SEQUENCE: 26

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
        35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Phe Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Ala Glu Asn Tyr Val Pro Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Val Asp Tyr Ala Lys Glu Ile Gly
    210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285

Asn Gly Val Leu Gly Ser Ile Asp Ala Asn Gln Gly Asp Met Leu Leu
    290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
    370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
            420                 425                 430

Asn Gln Tyr Leu Phe Ala Glu
        435

<210> SEQ ID NO 27
<211> LENGTH: 439
<212> TYPE: PRT
<213> ORGANISM: Thermoanaerobacterium saccharolyticum

<400> SEQUENCE: 27

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
                20                  25                  30

Ile Asp Gly Lys Thr Met Glu Glu His Leu Arg Phe Ser Ile Ala Tyr
            35                  40                  45

Trp His Thr Phe Thr Ala Asp Gly Thr Asp Gln Phe Gly Lys Ala Thr
        50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Phe Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
            165                 170                 175

Thr Lys Glu Leu Gly Ala Glu Asn Tyr Val Ser Trp Gly Gly Arg Glu
            180                 185                 190

Gly Tyr Glu Thr Leu Leu Asn Thr Asp Met Glu Leu Leu Asp Asn
            195                 200                 205

Phe Ala Arg Phe Leu His Met Ala Val Asp Tyr Ala Lys Glu Ile Gly
            210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
            245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
            275                 280                 285

Asn Gly Val Leu Gly Ser Ile Asp Ala Asn Ile Gly Asp Met Leu Leu
            290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
            325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
            355                 360                 365

Val Ala Tyr Lys Leu Val Lys Asp Gly Val Phe Asp Lys Phe Ile Glu
            370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
            405                 410                 415

Gln Ile Val Asn Lys Ser Gly Arg Gln Glu Leu Leu Glu Ser Ile Leu
            420                 425                 430

Asn Gln Tyr Leu Phe Ala Glu
            435

<210> SEQ ID NO 28
<211> LENGTH: 439
<212> TYPE: PRT
<213> ORGANISM: Thermoanaerobacterium saccharolyticum

<400> SEQUENCE: 28

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
            35                  40                  45

Trp His Thr Phe Thr Ala Asp Gly Thr Asp Gln Phe Gly Lys Ala Thr
            50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
            85                  90                  95

```
Phe Phe Cys Phe His Asp Arg Asp Ile Ala Pro Glu Gly Asp Thr Leu
                100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Phe Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Ala Glu Asn Tyr Val Ser Trp Gly Gly Arg Glu
        180                 185                 190

Gly Tyr Glu Thr Leu Leu Asn Thr Asp Met Glu Leu Glu Leu Asp Asn
    195                 200                 205

Phe Ala Arg Phe Leu His Met Ala Val Asp Tyr Ala Lys Glu Ile Gly
210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
        260                 265                 270

Thr Leu Ala Phe His Asp Phe Gln His Glu Leu Arg Tyr Ala Arg Ile
    275                 280                 285

Asn Gly Val Leu Gly Ser Ile Asp Ala Asn Tyr Gly Asp Met Leu Leu
290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
        340                 345                 350

Phe Leu Gly His Ile Ala Gly Met Asp Ala Phe Ala Lys Gly Phe Lys
    355                 360                 365

Val Ala Tyr Lys Leu Val Lys Asp Gly Val Phe Asp Lys Phe Ile Glu
370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
        420                 425                 430

Asn Gln Tyr Leu Phe Ala Glu
        435

<210> SEQ ID NO 29
<211> LENGTH: 439
<212> TYPE: PRT
<213> ORGANISM: Thermoanaerobacterium saccharolyticum

<400> SEQUENCE: 29

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30
```

```
Ile Asp Gly Lys Thr Met Glu Glu His Leu Arg Phe Ser Ile Ala Tyr
         35                  40                  45

Trp His Thr Phe Thr Ala Asp Gly Thr Asp Gln Phe Gly Lys Ala Thr
 50                  55                  60

Met Gln Arg Pro Trp Asn His Tyr Thr Asp Pro Met Asp Ile Ala Lys
 65                  70                  75                  80

Ala Arg Val Glu Ala Ala Phe Glu Phe Phe Asp Lys Ile Asn Ala Pro
                 85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
            115                 120                 125

Tyr Leu Lys Thr Ser Lys Thr Lys Val Leu Phe Gly Thr Ala Asn Leu
        130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Ala Glu Asn Tyr Val Ser Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Val Asp Tyr Ala Lys Glu Ile Gly
        210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285

Asn Gly Val Leu Gly Ser Ile Asp Ala Asn Cys Gly Asp Met Leu Leu
290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
            420                 425                 430

Asn Gln Tyr Leu Phe Ala Glu
        435
```

<210> SEQ ID NO 30
<211> LENGTH: 439
<212> TYPE: PRT
<213> ORGANISM: Thermoanaerobacterium saccharolyticum

<400> SEQUENCE: 30

```
Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
        35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Phe Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Ala Glu Asn Tyr Val Ser Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Val Asp Tyr Ala Lys Glu Ile Gly
    210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285

Asn Gly Val Leu Gly Ser Ile Asp Ala Asn Met Gly Asp Met Leu Leu
    290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
    370                 375                 380

Glu Arg Tyr Ala Ser Tyr Lys Glu Gly Ile Gly Ala Asp Ile Val Ser
```

```
                385                 390                 395                 400
Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
                420                 425                 430

Asn Gln Tyr Leu Phe Ala Glu
                435

<210> SEQ ID NO 31
<211> LENGTH: 439
<212> TYPE: PRT
<213> ORGANISM: Thermoanaerobacterium saccharolyticum

<400> SEQUENCE: 31

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
                20                  25                  30

Ile Asp Gly Lys Thr Met Glu Glu His Leu Arg Phe Ser Ile Ala Tyr
            35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
                85                  90                  95

Phe Phe Cys Phe His Asp Arg Asp Ile Ala Pro Glu Gly Asp Thr Leu
                100                 105                 110

Arg Glu Thr Asn Lys Asn Leu Asp Thr Ile Val Ala Met Ile Lys Asp
                115                 120                 125

Tyr Leu Lys Thr Ser Lys Thr Lys Val Leu Phe Gly Thr Ala Asn Leu
            130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Ala Glu Asn Tyr Val Ser Trp Gly Gly Arg Glu
                180                 185                 190

Gly Tyr Glu Thr Leu Leu Asn Thr Asp Met Glu Leu Glu Leu Asp Asn
            195                 200                 205

Phe Ala Arg Phe Leu His Met Ala Val Asp Tyr Ala Lys Glu Ile Gly
    210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
                260                 265                 270

Thr Leu Ala Phe His Asp Phe Gln His Glu Leu Arg Tyr Ala Arg Ile
            275                 280                 285

Asn Gly Val Leu Gly Ser Ile Asp Ala Asn Glu Gly Asp Met Leu Leu
    290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
```

```
                            325                 330                 335
Asn Phe Asp Ala Lys Val Arg Arg Ala Ser Phe Glu Pro Glu Asp Leu
                340                 345                 350

Phe Leu Gly His Ile Ala Gly Met Asp Ala Phe Ala Lys Gly Phe Lys
            355                 360                 365

Val Ala Tyr Lys Leu Val Lys Asp Gly Val Phe Asp Lys Phe Ile Glu
        370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
            420                 425                 430

Asn Gln Tyr Leu Phe Ala Glu
                435

<210> SEQ ID NO 32
<211> LENGTH: 439
<212> TYPE: PRT
<213> ORGANISM: Thermoanaerobacterium saccharolyticum

<400> SEQUENCE: 32

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
                20                  25                  30

Ile Asp Gly Lys Thr Met Glu Glu His Leu Arg Phe Ser Ile Ala Tyr
            35                  40                  45

Trp His Thr Phe Thr Ala Asp Gly Thr Asp Gln Phe Gly Lys Ala Thr
        50                  55                  60

Met Gln Arg Pro Trp Asn His Tyr Thr Asp Pro Met Asp Ile Ala Lys
65                  70                  75                  80

Ala Arg Val Glu Ala Ala Leu Glu Phe Phe Asp Lys Ile Asn Ala Pro
                85                  90                  95

Phe Phe Cys Phe His Asp Arg Asp Ile Ala Pro Glu Gly Asp Thr Leu
                100                 105                 110

Arg Glu Thr Asn Lys Asn Leu Asp Thr Ile Val Ala Met Ile Lys Asp
            115                 120                 125

Tyr Leu Lys Thr Ser Lys Thr Lys Val Leu Phe Gly Thr Ala Asn Leu
        130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Ala Glu Asn Tyr Val Ser Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Val Asp Tyr Ala Lys Glu Ile Gly
210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
```

```
                    260                 265                 270
Thr Leu Ala Phe His Asp Phe Gln His Glu Leu Arg Tyr Ala Arg Ile
            275                 280                 285

Asn Gly Val Leu Gly Ser Ile Asp Ala Asn Gln Gly Asp Met Leu Leu
            290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
            325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
            355                 360                 365

Val Ala Tyr Lys Leu Val Lys Asp Gly Val Phe Asp Lys Phe Ile Glu
            370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
            405                 410                 415

Gln Ile Val Asn Lys Ser Gly Arg Gln Glu Leu Leu Glu Ser Ile Leu
            420                 425                 430

Asn Gln Tyr Leu Phe Ala Glu
            435

<210> SEQ ID NO 33
<211> LENGTH: 439
<212> TYPE: PRT
<213> ORGANISM: Thermoanaerobacterium saccharolyticum

<400> SEQUENCE: 33

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
            35                  40                  45

Trp His Thr Phe Thr Ala Asp Gly Thr Asp Gln Phe Gly Lys Ala Thr
        50                  55                  60

Met Gln Arg Pro Trp Asn His Tyr Thr Asp Pro Met Asp Ile Ala Lys
65              70                  75                  80

Ala Arg Val Glu Ala Ala Met Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
            115                 120                 125

Tyr Leu Lys Thr Ser Lys Thr Lys Val Leu Phe Gly Thr Ala Asn Leu
        130                 135                 140

Phe Ser Asn Pro Arg Phe Val His Gly Ala Ser Thr Ser Cys Asn Ala
145             150                 155                 160

Asp Val Phe Ala Tyr Ser Ala Ala Gln Val Lys Lys Ala Leu Glu Ile
                165                 170                 175

Thr Lys Glu Leu Gly Ala Glu Asn Tyr Val Ser Trp Gly Gly Arg Glu
            180                 185                 190

Gly Tyr Glu Thr Leu Leu Asn Thr Asp Met Glu Leu Glu Leu Asp Asn
```

```
                195                 200                 205
Phe Ala Arg Phe Leu His Met Ala Val Asp Tyr Ala Lys Glu Ile Gly
        210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
        260                 265                 270

Thr Leu Ala Phe His Asp Phe Gln His Glu Leu Arg Tyr Ala Arg Ile
        275                 280                 285

Asn Gly Val Leu Gly Ser Ile Asp Ala Asn Gln Gly Asp Met Leu Leu
        290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
        340                 345                 350

Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
        370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
        420                 425                 430

Asn Gln Tyr Leu Phe Ala Glu
        435

<210> SEQ ID NO 34
<211> LENGTH: 439
<212> TYPE: PRT
<213> ORGANISM: Thermoanaerobacterium saccharolyticum

<400> SEQUENCE: 34

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
                20                  25                  30

Ile Asp Gly Lys Thr Met Glu His Leu Arg Phe Ser Ile Ala Tyr
            35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Phe Gly Thr Ala Asn Leu
```

```
                130                 135                 140
Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Ala Glu Asn Tyr Val Ser Trp Gly Gly Arg Glu
            180                 185                 190

Gly Tyr Glu Thr Leu Leu Asn Thr Asp Met Glu Leu Leu Asp Asn
            195                 200                 205

Phe Ala Arg Phe Leu His Met Ala Arg Asp Tyr Ala Lys Glu Ile Gly
210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285

Asn Gly Val Leu Gly Ser Ile Asp Ala Asn Gln Gly Asp Met Leu Leu
290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Ser Ile Leu
            420                 425                 430

Asn Gln Tyr Leu Phe Ala Glu
        435

<210> SEQ ID NO 35
<211> LENGTH: 439
<212> TYPE: PRT
<213> ORGANISM: Thermoanaerobacterium saccharolyticum

<400> SEQUENCE: 35

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
                20                  25                  30

Ile Asp Gly Lys Thr Met Glu Glu His Leu Arg Phe Ser Ile Ala Tyr
            35                  40                  45

Trp His Thr Phe Thr Ala Asp Gly Thr Asp Gln Phe Gly Lys Ala Thr
        50                  55                  60

Met Gln Arg Pro Trp Asn His Tyr Thr Asp Pro Met Asp Ile Ala Lys
```

```
            65                  70                  75                  80
Ala Arg Val Glu Ala Ala Phe Glu Phe Asp Lys Ile Asn Ala Pro
                        85                  90                  95

Phe Phe Cys Phe His Asp Arg Asp Ile Ala Pro Glu Gly Asp Thr Leu
                    100                 105                 110

Arg Glu Thr Asn Lys Asn Leu Asp Thr Ile Val Ala Met Ile Lys Asp
                    115                 120                 125

Tyr Leu Lys Thr Ser Lys Thr Lys Val Leu Phe Gly Thr Ala Asn Leu
            130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                        165                 170                 175

Thr Lys Glu Leu Gly Ala Glu Asn Tyr Val Ser Trp Gly Gly Arg Glu
                    180                 185                 190

Gly Tyr Glu Thr Leu Leu Asn Thr Asp Met Glu Leu Glu Leu Asp Asn
                    195                 200                 205

Phe Ala Arg Phe Leu His Met Ala Val Asp Tyr Ala Lys Glu Ile Gly
            210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                        245                 250                 255

Tyr Asp Leu Glu Lys Tyr Phe Lys Val Asn Ile Glu Ala Asn His Ala
                    260                 265                 270

Thr Leu Ala Phe His Asp Phe Gln His Glu Leu Arg Tyr Ala Arg Ile
                    275                 280                 285

Asn Gly Val Leu Gly Ser Ile Asp Ala Asn Gln Gly Asp Met Leu Leu
            290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                        325                 330                 335

Asn Phe Asp Ala Lys Val Arg Arg Ala Ser Phe Glu Pro Glu Asp Leu
                    340                 345                 350

Phe Leu Gly His Ile Ala Gly Met Asp Ala Phe Ala Lys Gly Phe Lys
                    355                 360                 365

Val Ala Tyr Lys Leu Val Lys Asp Gly Val Phe Asp Lys Phe Ile Glu
            370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                        405                 410                 415

Gln Ile Val Asn Lys Ser Gly Arg Gln Glu Leu Leu Glu Ser Ile Leu
                    420                 425                 430

Asn Gln Tyr Leu Phe Ala Glu
            435

<210> SEQ ID NO 36
<211> LENGTH: 439
<212> TYPE: PRT
<213> ORGANISM: Thermoanaerobacterium saccharolyticum

<400> SEQUENCE: 36

Met Asn Lys Tyr Phe Glu Asn Val Ser Lys Ile Lys Tyr Glu Gly Pro
```

-continued

```
1               5                   10                  15
Lys Ser Asn Asn Pro Tyr Ser Phe Lys Phe Tyr Asn Pro Glu Glu Val
                20                  25                  30

Ile Asp Gly Lys Thr Met Glu Glu His Leu Arg Phe Ser Ile Ala Tyr
                35                  40                  45

Trp His Thr Phe Thr Ala Asp Gly Thr Asp Gln Phe Gly Lys Ala Thr
                50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Asp Lys Ile Asn Ala Pro
                85                  90                  95

Phe Phe Cys Phe His Asp Arg Asp Ile Ala Pro Glu Gly Asp Thr Leu
                100                 105                 110

Arg Glu Thr Asn Lys Asn Leu Asp Thr Ile Val Ala Met Ile Lys Asp
                115                 120                 125

Tyr Leu Lys Thr Ser Lys Thr Lys Val Leu Phe Gly Thr Ala Asn Leu
                130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Ala Glu Asn Tyr Val Ser Trp Gly Gly Arg Glu
                180                 185                 190

Gly Tyr Glu Thr Leu Leu Asn Thr Asp Met Glu Leu Glu Leu Asp Asn
                195                 200                 205

Phe Ala Arg Phe Leu His Met Ala Val Asp Tyr Ala Lys Glu Ile Gly
                210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
                260                 265                 270

Thr Leu Ala Gly His Asp Phe Gln His Glu Leu Arg Tyr Ala Arg Ile
                275                 280                 285

Asn Gly Val Leu Gly Ser Ile Asp Ala Asn Gln Gly Asp Met Leu Leu
                290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
                340                 345                 350

Phe Leu Gly His Ile Ala Gly Met Asp Ala Phe Ala Lys Gly Phe Lys
                355                 360                 365

Val Ala Tyr Lys Leu Val Lys Asp Gly Val Phe Asp Lys Phe Ile Glu
                370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
                420                 425                 430
```

Asn Gln Tyr Leu Phe Ala Glu
        435

<210> SEQ ID NO 37
<211> LENGTH: 439
<212> TYPE: PRT
<213> ORGANISM: Thermoanaerobacterium saccharolyticum

<400> SEQUENCE: 37

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
        35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Leu Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Phe Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Ala Glu Asn Tyr Val Ser Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Val Asp Tyr Ala Lys Glu Ile Gly
    210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Ala Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285

Asn Gly Val Leu Gly Ser Ile Asp Ala Asn Gln Gly Asp Met Leu Leu
    290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
        355                 360                 365

```
Val Ala Tyr Lys Leu Val Lys Asp Gly Val Phe Asp Lys Phe Ile Glu
            370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
                420                 425                 430

Asn Gln Tyr Leu Phe Ala Glu
                435

<210> SEQ ID NO 38
<211> LENGTH: 439
<212> TYPE: PRT
<213> ORGANISM: Thermoanaerobacterium saccharolyticum

<400> SEQUENCE: 38

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
                20                  25                  30

Ile Asp Gly Lys Thr Met Glu Glu His Leu Arg Phe Ser Ile Ala Tyr
            35                  40                  45

Trp His Thr Phe Thr Ala Asp Gly Thr Asp Gln Phe Gly Lys Ala Thr
 50                  55                  60

Met Gln Arg Pro Trp Asn His Tyr Thr Asp Pro Met Asp Ile Ala Lys
65                  70                  75                  80

Ala Arg Val Glu Ala Ala Leu Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Phe Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Ala Glu Asn Tyr Val Ser Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Val Asp Tyr Ala Lys Glu Ile Gly
210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Thr His Asp Phe Gln His Glu Leu Arg Tyr Ala Arg Ile
        275                 280                 285

Asn Gly Val Leu Gly Ser Ile Asp Ala Asn Gln Gly Asp Met Leu Leu
    290                 295                 300
```

```
Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
            420                 425                 430

Asn Gln Tyr Leu Phe Ala Glu
            435

<210> SEQ ID NO 39
<211> LENGTH: 439
<212> TYPE: PRT
<213> ORGANISM: Thermoanaerobacterium saccharolyticum

<400> SEQUENCE: 39

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
                20                  25                  30

Ile Asp Gly Lys Thr Met Glu Glu His Leu Arg Phe Ser Ile Ala Tyr
            35                  40                  45

Trp His Thr Phe Thr Ala Asp Gly Thr Asp Gln Phe Gly Lys Ala Thr
        50                  55                  60

Met Gln Arg Pro Trp Asn His Tyr Thr Asp Pro Met Asp Ile Ala Lys
65                  70                  75                  80

Ala Arg Val Glu Ala Ala Leu Glu Phe Phe Asp Lys Ile Asn Ala Pro
                85                  90                  95

Phe Phe Cys Phe His Asp Arg Asp Ile Ala Pro Glu Gly Asp Thr Leu
                100                 105                 110

Arg Glu Thr Asn Lys Asn Leu Asp Thr Ile Val Ala Met Ile Lys Asp
            115                 120                 125

Tyr Leu Lys Thr Ser Lys Thr Lys Val Leu Phe Gly Thr Ala Asn Leu
        130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Ala Glu Asn Tyr Val Ser Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Gly Asp Tyr Ala Lys Glu Ile Gly
        210                 215                 220

Phe Glu Gly Gln Phe Leu Ile Glu Pro Lys Pro Lys Glu Pro Thr Lys
225                 230                 235                 240
```

```
His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Thr His Asp Phe Gln His Glu Leu Arg Tyr Ala Arg Ile
        275                 280                 285

Asn Gly Val Leu Gly Ser Ile Asp Ala Asn Gln Gly Asp Met Leu Leu
    290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
    370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
            420                 425                 430

Asn Gln Tyr Leu Phe Ala Glu
            435

<210> SEQ ID NO 40
<211> LENGTH: 439
<212> TYPE: PRT
<213> ORGANISM: Thermoanaerobacterium saccharolyticum

<400> SEQUENCE: 40

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
        35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Leu Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Phe Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175
```

```
Thr Lys Glu Leu Gly Ala Glu Asn Tyr Val Ser Trp Gly Gly Arg Glu
            180                 185                 190

Gly Tyr Glu Thr Leu Leu Asn Thr Asp Met Glu Leu Glu Leu Asp Asn
            195                 200                 205

Phe Ala Arg Phe Leu His Met Ala Gly Asp Tyr Ala Lys Glu Ile Gly
            210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Ala Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
            275                 280                 285

Asn Gly Val Leu Gly Ser Ile Asp Ala Asn Gln Gly Asp Met Leu Leu
            290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
            325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
            355                 360                 365

Val Ala Tyr Lys Leu Val Lys Asp Gly Val Phe Asp Lys Phe Ile Glu
            370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
            420                 425                 430

Asn Gln Tyr Leu Phe Ala Glu
            435
```